(12) United States Patent
Harlev et al.

(10) Patent No.: US 11,728,026 B2
(45) Date of Patent: Aug. 15, 2023

(54) THREE-DIMENSIONAL CARDIAC REPRESENTATION

(71) Applicant: Affera, Inc., Watertown, MA (US)

(72) Inventors: Doron Harlev, Brookline, MA (US); Geoffrey Peter Wright, Boston, MA (US)

(73) Assignee: AFFERA, INC., Watertown, MA (US)

( * ) Notice: Subject to any disclaimer, the term of this patent is extended or adjusted under 35 U.S.C. 154(b) by 754 days.

(21) Appl. No.: 15/594,039

(22) Filed: May 12, 2017

(65) Prior Publication Data

US 2017/0330487 A1   Nov. 16, 2017

Related U.S. Application Data

(60) Provisional application No. 62/463,870, filed on Feb. 27, 2017, provisional application No. 62/410,022, (Continued)

(51) Int. Cl.
*G16H 30/40* (2018.01)
*A61B 34/00* (2016.01)
(Continued)

(52) U.S. Cl.
CPC ......... *G16H 30/40* (2018.01); *A61B 18/1492* (2013.01); *A61B 34/10* (2016.02); *A61B 34/20* (2016.02); *A61B 34/25* (2016.02); *G06F 3/04815* (2013.01); *G06F 3/04845* (2013.01); *G06F 3/04847* (2013.01); *G09B 5/02* (2013.01); *G09B 23/30* (2013.01); *G16H 15/00* (2018.01); *G16H 30/20* (2018.01); *A61B 2018/00357* (2013.01); *A61B 2018/00577* (2013.01); *A61B 2034/105* (2016.02);
(Continued)

(58) Field of Classification Search
CPC ......... A61B 34/25; A61B 34/10; A61B 34/20; G16H 15/00; G06F 3/04815; G06F 3/04845
See application file for complete search history.

(56) References Cited

U.S. PATENT DOCUMENTS 4,734,690 A   3/1988   Waller
5,133,336 A   7/1992   Savitt
(Continued)

FOREIGN PATENT DOCUMENTS

EP   1793349 A2   6/2007
EP   1837828 B1   9/2007
(Continued)

OTHER PUBLICATIONS

3D-Doctor User's Manual: 3D Imaging, Modeling and Measurement Software (2012) (pp. 1-269).*
(Continued)

*Primary Examiner* — Sarah Lhymn
(74) *Attorney, Agent, or Firm* — Tarolli, Sundheim, Covell & Tummino L.L.P.

(57) ABSTRACT

Systems and methods of the present disclosure are directed to controlling the build of a three-dimensional model of a cardiac chamber. More specifically, the systems and methods of the present disclosure can be used to rewind a portion of a construction of a three-dimensional model of the cardiac chamber.

14 Claims, 14 Drawing Sheets

Related U.S. Application Data filed on Oct. 19, 2016, provisional application No. 62/384,291, filed on Sep. 7, 2016, provisional application No. 62/338,210, filed on May 18, 2016, provisional application No. 62/336,143, filed on May 13, 2016, provisional application No. 62/335,120, filed on May 12, 2016.

(51) Int. Cl.

| | | |
|---|---|---|
| *G09B 23/30* | (2006.01) | |
| *A61B 34/20* | (2016.01) | |
| *A61B 18/14* | (2006.01) | |
| *A61B 34/10* | (2016.01) | |
| *G06F 3/04847* | (2022.01) | |
| *G06F 3/04815* | (2022.01) | |
| *G16H 15/00* | (2018.01) | |
| *G16H 30/20* | (2018.01) | |
| *G09B 5/02* | (2006.01) | |
| *G06F 3/04845* | (2022.01) | |
| *A61B 18/00* | (2006.01) | |
| *G06F 3/02* | (2006.01) | |
| *G06F 3/0482* | (2013.01) | |

(52) U.S. Cl.
CPC . *A61B 2034/2065* (2016.02); *A61B 2034/252* (2016.02); *G06F 3/0202* (2013.01); *G06F 3/0482* (2013.01)

(56) References Cited

U.S. PATENT DOCUMENTS

| | | |
|---|---|---|
| 5,276,785 A | 1/1994 | Mackinlay et al. |
| 5,364,395 A | 11/1994 | West |
| 5,391,199 A | 2/1995 | Ben-Haim |
| 5,433,198 A | 7/1995 | Desai |
| 5,447,529 A | 9/1995 | Marchlinski et al. |
| 5,623,583 A | 4/1997 | Nichino |
| 5,655,535 A | 8/1997 | Friemel et al. |
| 5,687,737 A | 11/1997 | Branham et al. |
| 5,797,849 A | 8/1998 | Vesely et al. |
| 5,820,568 A | 10/1998 | Willis |
| 5,889,524 A | 3/1999 | Sheehan et al. |
| 6,037,937 A | 3/2000 | Beaton |
| 6,120,435 A | 9/2000 | Eino |
| 6,120,496 A | 9/2000 | Whayne et al. |
| 6,175,655 B1 | 1/2001 | George, III et al. |
| 6,216,027 B1 | 4/2001 | Willis |
| 6,256,038 B1 | 7/2001 | Krishnamurthy |
| 6,271,856 B1 | 8/2001 | Krishnamurthy |
| 6,304,267 B1 | 10/2001 | Sata |
| 6,377,865 B1 | 4/2002 | Edelsbrunner et al. |
| 6,443,894 B1 | 9/2002 | Sumanaweera et al. |
| 6,556,206 B1 | 4/2003 | Benson et al. |
| 6,572,611 B1 | 6/2003 | Falwell |
| 6,664,986 B1 | 12/2003 | Kopelman et al. |
| 6,961,911 B2 | 11/2005 | Suzuki |
| 6,968,299 B1 | 11/2005 | Bernardini et al. |
| 7,023,432 B2 | 4/2006 | Fletcher et al. |
| 7,092,773 B1* | 8/2006 | Oliver ............... G11B 27/034 360/13 |
| 7,155,042 B1 | 12/2006 | Cowan |
| 7,285,117 B2 | 10/2007 | Krueger |
| 7,315,638 B2 | 1/2008 | Hara |
| 7,365,745 B2 | 4/2008 | Olson |
| 7,450,749 B2 | 11/2008 | Rouet et al. |
| 7,656,418 B2 | 2/2010 | Watkins et al. |
| 7,714,856 B2 | 5/2010 | Waldinger et al. |
| 7,894,663 B2 | 2/2011 | Berg et al. |
| 8,014,561 B2 | 9/2011 | Farag et al. |
| 8,334,867 B1 | 12/2012 | Davidson |
| 8,636,729 B2 | 1/2014 | Brady et al. |
| 8,784,413 B2 | 7/2014 | Schwartz |
| 8,786,594 B2 | 7/2014 | Kushwaha et al. |
| 8,817,076 B2 | 8/2014 | Steen |
| 8,920,368 B2 | 12/2014 | Sandhu et al. |
| 9,211,160 B2 | 12/2015 | Pivotto et al. |
| 9,245,382 B2 | 1/2016 | Zhou et al. |
| 9,256,980 B2 | 2/2016 | Kirk |
| 9,311,744 B2 | 4/2016 | Wu et al. |
| 9,358,076 B2 | 6/2016 | Moll |
| 9,439,736 B2 | 9/2016 | Olson |
| 9,613,291 B2 | 4/2017 | Wu et al. |
| 9,888,973 B2 | 2/2018 | Olson et al. |
| 10,163,252 B2 | 12/2018 | Harlev |
| 10,376,320 B2 | 8/2019 | Harlev |
| 2002/0062083 A1 | 5/2002 | Ohara |
| 2002/0062084 A1 | 5/2002 | Ohara |
| 2002/0165541 A1 | 11/2002 | Whitman |
| 2003/0032862 A1 | 2/2003 | Ota |
| 2003/0060831 A1 | 3/2003 | Bonutti |
| 2003/0176778 A1 | 9/2003 | Messing |
| 2003/0189567 A1 | 10/2003 | Baumberg |
| 2003/0229282 A1* | 12/2003 | Burdette ............... A61B 8/12 600/439 |
| 2004/0043368 A1 | 3/2004 | Hsieh |
| 2004/0233222 A1 | 11/2004 | Lee et al. |
| 2004/0249809 A1 | 12/2004 | Ramani |
| 2005/0128184 A1 | 6/2005 | McGreevy |
| 2006/0159323 A1 | 7/2006 | Sun |
| 2006/0203089 A1 | 9/2006 | Akimoto |
| 2006/0241445 A1 | 10/2006 | Altmann et al. |
| 2007/0038088 A1 | 2/2007 | Rich et al. |
| 2007/0203396 A1 | 8/2007 | McCutcheon et al. |
| 2007/0208260 A1 | 9/2007 | Afonso |
| 2007/0220444 A1 | 9/2007 | Sunday et al. |
| 2007/0299351 A1 | 12/2007 | Harlev |
| 2007/0299352 A1 | 12/2007 | Harlev |
| 2007/0299353 A1 | 12/2007 | Harlev |
| 2008/0138009 A1 | 6/2008 | Block et al. |
| 2008/0161681 A1 | 7/2008 | Hauck |
| 2008/0221425 A1 | 9/2008 | Olson |
| 2008/0221438 A1 | 9/2008 | Chen |
| 2008/0270095 A1* | 10/2008 | Lombaert ............ A61B 5/7289 703/11 |
| 2008/0308256 A1 | 12/2008 | Deborski |
| 2009/0076476 A1 | 3/2009 | Barbagli et al. |
| 2009/0163810 A1 | 6/2009 | Kanade et al. |
| 2009/0171274 A1 | 7/2009 | Harlev |
| 2009/0177111 A1 | 7/2009 | Miller |
| 2009/0264741 A1* | 10/2009 | Markowitz .......... A61B 5/4836 600/424 |
| 2009/0264742 A1 | 10/2009 | Markowitz |
| 2009/0281418 A1 | 11/2009 | Ruitjers et al. |
| 2010/0053208 A1 | 3/2010 | Menningen et al. |
| 2010/0069921 A1 | 3/2010 | Miller et al. |
| 2010/0100081 A1 | 4/2010 | Tuma |
| 2010/0106009 A1 | 4/2010 | Harlev |
| 2010/0168560 A1 | 7/2010 | Hauck |
| 2010/0256558 A1 | 10/2010 | Ols |
| 2010/0259542 A1 | 10/2010 | Visser et al. |
| 2010/0305427 A1 | 12/2010 | Huber |
| 2010/0317981 A1 | 12/2010 | Grunwald |
| 2011/0015533 A1 | 1/2011 | Cox et al. |
| 2011/0034971 A1 | 2/2011 | Svanberg |
| 2011/0058653 A1 | 3/2011 | Baumgart et al. |
| 2011/0060762 A1* | 3/2011 | Bessette ............... G06Q 50/22 707/770 |
| 2011/0112569 A1 | 5/2011 | Friedman |
| 2011/0144806 A1 | 6/2011 | Sandhu et al. |
| 2011/0152684 A1 | 6/2011 | Altmann et al. |
| 2011/0175990 A1 | 7/2011 | Sato |
| 2011/0236868 A1 | 9/2011 | Bronstein |
| 2011/0243323 A1 | 10/2011 | Sato |
| 2012/0004540 A1 | 1/2012 | Liu et al. |
| 2012/0059249 A1 | 3/2012 | Verard et al. |
| 2012/0089038 A1 | 4/2012 | Ryu |
| 2012/0097178 A1* | 4/2012 | Helm .................. A61B 6/032 128/898 |
| 2012/0123404 A1 | 5/2012 | Craig |
| 2012/0165810 A1 | 6/2012 | Gillberg et al. |
| 2012/0169857 A1 | 7/2012 | Sato |
| 2012/0174022 A1 | 7/2012 | Sandhu et al. |

(56) References Cited

U.S. PATENT DOCUMENTS

| | | | |
|---|---|---|---|
| 2012/0177269 A1* | 7/2012 | Lu .................... | G06K 9/4609 382/131 |
| 2012/0221569 A1 | 8/2012 | Sato | |
| 2012/0245465 A1 | 9/2012 | Hansegard et al. | |
| 2013/0002968 A1 | 1/2013 | Bridge et al. | |
| 2013/0030285 A1 | 1/2013 | Vaillant | |
| 2013/0033519 A1 | 2/2013 | Sato | |
| 2013/0129170 A1 | 5/2013 | Zheng | |
| 2013/0241929 A1 | 9/2013 | Massaeawa et al. | |
| 2013/0286012 A1 | 10/2013 | Medioni | |
| 2014/0100453 A1* | 4/2014 | Kemp ................ | A61B 5/0084 600/425 |
| 2014/0328524 A1 | 11/2014 | Calabrese | |
| 2015/0018698 A1 | 1/2015 | Safran | |
| 2015/0042657 A1 | 2/2015 | Smith-Casem | |
| 2015/0057529 A1 | 2/2015 | Merschon | |
| 2015/0119735 A1 | 4/2015 | Yang | |
| 2015/0272464 A1 | 10/2015 | Armoundas | |
| 2015/0324114 A1 | 11/2015 | Hurley et al. | |
| 2016/0000300 A1 | 1/2016 | Williams | |
| 2016/0073928 A1 | 3/2016 | Soper et al. | |
| 2016/0147308 A1 | 5/2016 | Gelman | |
| 2016/0174865 A1 | 6/2016 | Stewart et al. | |
| 2016/0196666 A1 | 7/2016 | Venkatraghavan et al. | |
| 2016/0242667 A1 | 8/2016 | Fay et al. | |
| 2016/0242855 A1 | 8/2016 | Fichtinger et al. | |
| 2016/0275653 A1 | 9/2016 | Ross | |
| 2016/0331262 A1 | 11/2016 | Kuck et al. | |
| 2016/0364862 A1* | 12/2016 | Reicher ................ | G06F 19/00 |
| 2016/0367168 A1 | 12/2016 | Malinin et al. | |
| 2017/0038951 A1* | 2/2017 | Reicher ................ | G06F 16/245 |
| 2017/0065256 A1 | 3/2017 | Kim et al. | |
| 2017/0079542 A1 | 3/2017 | Spector | |
| 2017/0079681 A1 | 3/2017 | Burnside et al. | |
| 2017/0202469 A1* | 7/2017 | Scharf ................ | A61B 8/445 |
| 2017/0209072 A1 | 7/2017 | Oren | |
| 2017/0245936 A1 | 8/2017 | Kanade et al. | |
| 2017/0265943 A1 | 9/2017 | Sela et al. | |
| 2017/0301124 A1 | 10/2017 | Dala-Krishna | |
| 2017/0323473 A1 | 11/2017 | Wright | |
| 2017/0325900 A1 | 11/2017 | Harlev et al. | |
| 2017/0325901 A1 | 11/2017 | Harlev et al. | |
| 2018/0228386 A1 | 8/2018 | McCall | |
| 2018/0289435 A1 | 10/2018 | Namiki | |
| 2018/0317864 A1 | 11/2018 | Sra et al. | |
| 2019/0004621 A1 | 1/2019 | Nuber et al. | |
| 2019/0030328 A1 | 1/2019 | Stewart et al. | |
| 2019/0096122 A1 | 3/2019 | Harlev | |
| 2019/0125422 A1 | 5/2019 | Babkin et al. | |
| 2019/0269368 A1 | 9/2019 | Hauck et al. | |
| 2020/0196908 A1 | 6/2020 | Ben-Haim et al. | |
| 2021/0022623 A1 | 1/2021 | Rice et al. | |

FOREIGN PATENT DOCUMENTS

| | | |
|---|---|---|
| EP | 2332461 A1 | 6/2011 |
| WO | WO-03039350 | 5/2003 |
| WO | 2005022468 A1 | 3/2005 |
| WO | 2005063125 A1 | 7/2005 |
| WO | WO-2008107905 | 9/2008 |
| WO | 2008138009 A1 | 11/2008 |
| WO | 2010054409 A1 | 5/2010 |
| WO | 2017192746 A1 | 11/2017 |
| WO | 2017192781 A1 | 11/2017 |
| WO | 2017197114 A1 | 11/2017 |
| WO | 2017197247 A1 | 11/2017 |
| WO | WO-2017197294 | 11/2017 |
| WO | 2018092063 A1 | 5/2018 |
| WO | 2018200865 A1 | 11/2018 |
| WO | 2019046376 A1 | 3/2019 |

OTHER PUBLICATIONS

ISA, "PCT Application No. PCT/US17/32378 International Search Report and Written Opinion dated Dec. 20, 2017", 17 pages.

ISA, "PCT Application No. PCT/US17/32378 Invitation to Pay Additional Fees and Partial Search Report dated Oct. 23, 2017", 15 pages.

ISA, "PCT Application No. PCT/US17/32459 International Search Report and Written Opinion dated Jul. 21, 2017", 11 pages.

"Framing (World Wide Web)", published by Wikipeda, [online] https://en.wikipedia.org/wiki/Framing_(World_Wide_Web) (Year: 2018).

Bernardini, Fausto et al., "The Ball-Pivoting Algorithm for Surface Reconstruction", IEEE transactions on visualization and computer graphics 5.4 (1999), Oct. 1999, pp. 349-359.

Carr, J.C. et al., "Reconstruction and Representation of 3D Objects with Radial Basis Functions", Proceedings of the 28th annual conference on Computer graphics and interactive techniques. ACM, 2001, 10 Pages.

Chen, Yang et al., "Description of Complex Objects from Multiple Range Images Using an Inflating Balloon Model", Computer Vision and Image Understanding 61.3, May 1995, pp. 325-334.

Curless, Brian et al., "A Volumetric Method for Building Complex Models from Range Images", Proceedings of the 23rd annual conference on Computer graphics and interactive techniques. ACM, 1996, 10 Pages.

Davis, James et al., "Filling holes in complex surfaces using volumetric diffusion", 3D Data Processing Visualization and Transmission, 2002. Proceedings. First International Symposium on. IEEE, 2002, 15 Pages.

Elfes, Alberto, "Using Occupancy Grids for Mobile Robot Perception and Navigation", Computer, vol. 22, Issue: 6, Jun. 1989, pp. 46-57.

Gelas, Arnaud et al., "Surface Meshes Smoothing", Insight Journal. Feb. 20, 2009, 6 Pages.

Hilbert, Sebastian et al., "Real-Time Magnetic Resonance-guided ablation of typical right atrial flutter using a combination of active catheter tracking and passive catheter visualization in main: initial results from a consecutive patient series", Aug. 27, 2015, 6 pages.

ISA, "PCT Application No. PCT/US17/30877 International Search Report and Written Opinion dated Jul. 14, 2017", 9 pages.

ISA, "PCT Application No. PCT/US17/30928 International Search Report and Written Opinion dated Jul. 25, 2017", 12 pages.

ISA, "PCT Application No. PCT/US17/32160 International Search Report and Written Opinion dated Aug. 21, 2017", 8 pages.

ISA, "PCT Application No. PCTUS18/48460, International Search Report and Written Opinion dated Feb. 1, 2019", 19 pages.

Kazhdan, Michael et al., "Poisson Surface Reconstruction", Eurographics Symposium on Geometry Processing, 2006, 10 Pages.

Lempitsky, Victor, "Surface Extraction from Binary Volumes with Higher-Order Smoothness", Computer Vision and Pattern Recognition (CVPR), 2010 IEEE Conference on. IEEE, Jun. 2010, 6 Pages.

Liang, Jian et al., "Robust and Efficient Implicit Surface Reconstruction for Point Clouds Based on Convexified Image Segmentation", Journal of Scientific Computing 54.2-3, 2013, pp. 577-602.

Lounsbery, Michael et al., "Parametric Surface Interpolation", IEEE Computer Graphics and Applications 12.5 (1992) Sep. 1992, pp. 45-52.

Schroeder, William et al., "Flying Edges: A High-Performance Scalable Isocontouring Algorithm", IEEE Xplore, Oct. 2015, 8 pages.

Sethian, J.A., "Level Set Methods and Fast Marching Methods", Cambridge University Press, 1996, 21 Pages.

Wang, Jianning et al., "A Hole-Filling Strategy for Reconstruction of Smooth Surfaces in Range Images", Computer Graphics and Image Processing, 2003. SIBGRAPI 2003. XVI Brazilian Symposium on. IEEE, Oct. 2003, 7 pages.

Zhao, Hong-Kai et al., "Fast Surface Reconstruction Using the Level Set Method", Variational and Level Set Methods in Computer Vision, 2001. Proceedings. IEEE Workshop on. IEEE, Jul. 2001, 8 pages.

ISA, "PCT Application No. PCTUS20/14850, International Search Report and Written Opinion dated Apr. 7, 2020", 14 pages.

(56) References Cited

OTHER PUBLICATIONS

Lange et al., 3D Ultrasound-CT registration of the liver using combined landmark-intensity information, International Journal of Computer Assisted Radiology and Surgery, 4(1):79-88, 2008.

* cited by examiner

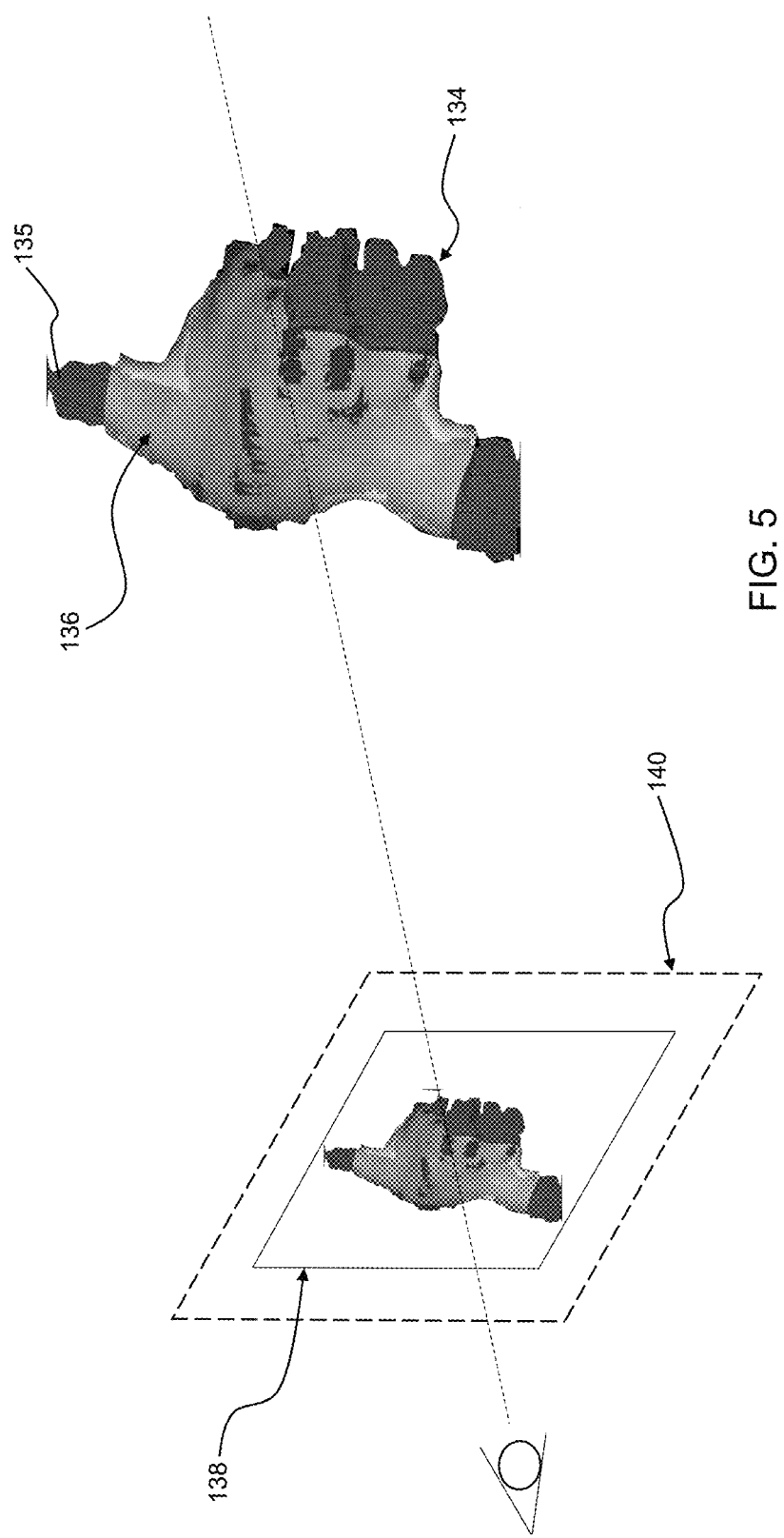

THREE-DIMENSIONAL CARDIAC REPRESENTATION

CROSS-REFERENCE TO RELATED APPLICATIONS

This application claims the benefit under 35 U.S.C. § 119(e) of U.S. Prov. App. No. 62/335,120, filed May 12, 2016, U.S. Prov. App. No. 62/336,143, filed May 13, 2016, U.S. Prov. App. 62/338,210, filed May 18, 2016, U.S. Prov. App. No. 62/384,291, filed Sep. 7, 2016, U.S. Prov. App. No. 62/410,022, filed Oct. 19, 2016, and U.S. Prov. App. No. 62/463,870, filed Feb. 27, 2017, with the entire contents of each of these applications hereby incorporated herein by reference.

This application is also related to commonly-owned U.S. patent application Ser. No. 15/593,778, filed on even date herewith and entitled "ANATOMICAL MODEL CONTROLLING," the entire contents of which are hereby incorporated herein by reference.

BACKGROUND

Three-dimensional models can be used to assist in the placement or use of a device when such placement or use is not easily observable. For example, in medical procedures, three-dimensional models are used to assist in the placement and use of medical devices used for diagnosis or treatment of patients. An example of such a medical procedure carried out with the assistance of a three-dimensional model is the use of a catheter to deliver radio frequency ("RF") ablation to form lesions that interrupt abnormal conduction in cardiac tissue, thus terminating certain arrhythmias in the heart.

SUMMARY

The present disclosure is directed to devices, systems, and methods of controlling the construction of a three-dimensional model of a cardiac chamber. More specifically, the devices, systems, and methods of the present disclosure can be used to rewind a portion of a build of a three-dimensional model of the cardiac chamber. As compared to systems and methods that do not offer a physician the ability to rewind a build of a three-dimensional model of a cardiac chamber, the systems and methods of the present disclosure can facilitate efficiently building an accurate representation of the cardiac chamber, which can reduce the time of a medical procedure. Additionally, or alternatively, the accuracy in building the representation of the cardiac chamber can be useful for visualizing movement of a medical device in the cardiac chamber.

According to one aspect, a method includes receiving a plurality of signals indicative of respective visited locations of a catheter in a cardiac chamber of a patient, progressively forming, based on the visited locations of the catheter in the cardiac chamber, a continuous surface representing at least a portion of a surface of the cardiac chamber, displaying the continuous surface on a graphical user interface, receiving, from an input device, a rewind command, and updating, based on the rewind command, a display of the continuous surface on the graphical user interface from a first state of the continuous surface to a second state of the continuous surface, at least a portion of the second state preceding at least a portion of the first state in the progressive formation of the continuous surface.

In some implementations, the first state of the continuous surface and the second state of the continuous surface can correspond to partially overlapping time periods in the progressive formation of the continuous surface.

In certain implementations, the first state of the continuous surface can define a first volume and the second state of the continuous surface can define a second volume different from the first volume. For example, the second volume can be less than the first volume. Additionally, or alternatively, receiving the rewind command can include receiving a signal indicative of a quantity of discrete inputs, and the difference between the first volume defined by the first state of the continuous surface and the second volume defined by the second state of the continuous surface can be substantially proportional to the quantity of discrete inputs. Each discrete input can, for example, correspond substantially to a predetermined difference in volume defined by the continuous surface.

In some implementations, the method can further include storing a plurality of temporal states of the continuous surface in a data structure, the plurality of temporal states of the continuous surface including the first state and the second state. For example, in the data structure, consecutive temporal states of the continuous surface can be distinguished from one another by a respective key frame based on a change in the continuous surface as the continuous surface is progressively formed. Further, or instead, the continuous surface corresponding to each state of the plurality of states can define a respective volume, and each key frame corresponds substantially to a predetermined change (e.g., about 1 cm$^3$) in volume between respective consecutive temporal states of the continuous surface.

In certain implementations, the data structure can include respective pointers corresponding to the first state of the continuous surface and the second state of the continuous surface, and displaying the second state of the continuous surface can include changing from a first pointer corresponding to the first state to a second pointer corresponding to the second state.

In some implementations, the data structure can include a three-dimensional data structure (e.g., a three-dimensional grid), and each state of the plurality of temporal states of the continuous surface can be derived from one or more portions of the three-dimensional data structure. The portions of the three-dimensional data structure can include, for example, surface elements forming the plurality of temporal states of the continuous surface. Additionally, or alternatively, the portions of the three-dimensional data structure can include one or more of zero-dimensional elements, one-dimensional elements, two-dimensional elements, three-dimensional elements, four-dimensional elements, and combinations thereof. By way of example, the first state of the continuous surface can be derived from the three-dimensional data structure corresponding to a first time period, the second state of the continuous surface can be derived from the three-dimensional data structure corresponding to a second time period, and at least a portion of the second time period can precede at least a portion of the first time period. The one or more portions of the three-dimensional data structure can be, in some instances, modified based on the rewind command.

In certain implementations, progressively forming the continuous surface can be based on a chronological order of the visited locations of the catheter in the cardiac chamber.

In some implementations, the method can further include receiving an undo command and, based on the undo command, modifying the display of the continuous surface on the graphical user interface from the second state of the continuous surface to a third state of the continuous surface, wherein the third state of the continuous surface follows the second state of the continuous surface in the progressive formation of the continuous surface. The third state of the continuous surface can precede or be substantially contemporaneous with the first state of the continuous surface in the progressive formation of the continuous surface.

According to another aspect, a method includes receiving a plurality of signals indicative of respective visited locations of a catheter in a cardiac chamber of a patient, displaying, on a graphical user interface, a continuous surface representing at least a portion of a surface of the cardiac chamber, the continuous surface derived from a data structure and based on the visited locations, receiving, from an input device, a rewind command, accessing, based on the rewind command and on an order of receipt of the visited locations of the catheter, one or more entries in the data structure, and, based on the accessed one or more entries in the data structure, updating the display of the continuous surface on the graphical user interface.

In some implementations, the method can further include forming, based on the visited locations of the catheter in the cardiac chamber, the data structure as a three-dimensional data structure of the visited catheter locations.

In certain implementations, accessing the one or more entries in the data structure can include removing the one or more entries from the data structure.

In some implementations, accessing the one or more entries of the data structure can include modifying the one or more entries corresponding to the visited locations of the catheter.

In certain implementations, accessing the one or more entries of the data structure can include modifying the one or more entries based on a reverse chronological order of receipt of the corresponding visited location or locations of the catheter. For example, accessing the one or more entries of the data structure can include modifying the one or more entries corresponding to the visited location or locations of the catheter based on a last-in-first-out priority. Additionally, or alternatively, accessing the one or more entries of the data structure can include removing the one or more entries corresponding to the most recently received location or locations of the catheter within a predetermined period.

In some implementations, receiving the rewind command can include receiving a signal indicative of a quantity of discrete inputs, and a quantity of the one or more accessed entries of the data structure is proportional to the quantity of the discrete inputs. For example, the quantity of discrete inputs can correspond to a received quantity of clicks of a click-based input device.

In certain implementations, receiving the rewind command can include displaying, on the graphical user interface, visual indicia of the received rewind command. Displaying visual indicia on the graphical user interface can include, for example, displaying a spatial extent of the received rewind command. As a more specific example, the spatial extent of the received rewind command can be displayed on one or more of the continuous surface, on the data structure, as a surface or volume separate from the continuous surface and the data structure, and combinations thereof. Further, or instead, displaying visual indicia on the graphical user interface can include displaying a temporal extent of the received rewind command, the temporal extent corresponding to a time between a first state of the continuous surface and a second state of the continuous surface, wherein the second state precedes the first state in a progressive formation of the continuous surface.

In some implementations, the method can further include receiving an undo command (e.g., from an input device) and, based on the undo command, modifying the display of the continuous surface from a second state of the continuous surface to a third state of the continuous surface, wherein the third state of the continuous surface follows the second state in a progressive formation of the continuous surface. The third state of the continuous surface can, for example, precede or be substantially contemporaneous with a first state of the continuous surface in the progressive formation of the continuous surface. Further or instead, receiving the undo command can include receiving a signal indicative of a quantity of discrete inputs (e.g., corresponding to a receive quantity of clicks of a click-based input device) and the third state of the continuous surface is based on the quantity of the discrete inputs.

According to another aspect, a non-transitory, computer-readable storage medium has stored thereon computer executable instructions for causing one or more processors to receive a plurality of signals indicative of respective visited locations of a catheter in a cardiac chamber of a patient, based on the visited locations of the catheter in the cardiac chamber, progressively form a continuous surface representing at least a portion of a surface of the cardiac chamber, display the continuous surface on a graphical user interface, receive, from an input device, a rewind command, and, based on the rewind command, update a display of the continuous surface on the graphical user interface from a first state of the continuous surface to a second state of the continuous surface, at least a portion of the second state preceding at least a portion of the first state in the progressive formation of the continuous surface.

According to still another aspect, a system includes a cardiac catheter and a computer interface unit in communication with the cardiac catheter. The catheter interface unit includes a graphical user interface, one or more processors, and a non-transitory, computer-readable storage medium having stored thereon computer executable instructions for causing one or more processors to receive a plurality of signals indicative of respective visited locations of a catheter in a cardiac chamber of a patient, based on the visited locations of the catheter in the cardiac chamber, progressively form a continuous surface representing at least a portion of a surface of the cardiac chamber, display the continuous surface on the graphical user interface, receive, from an input device, a rewind command, and, based on the rewind command, update a display of the continuous surface on the graphical user interface from a first state of the continuous surface to a second state of the continuous surface, at least a portion of the second state preceding at least a portion of the first state in the progressive formation of the continuous surface.

Implementations can include one or more of the following advantages.

In some implementations, a rewind command can facilitate editing a three-dimensional anatomic model formed based on catheter locations in a cardiac chamber. For example, the rewind command can facilitate efficient editing of the three-dimensional anatomic model as the model is being built. More specifically, the rewind command can correct distortions or errors in the three-dimensional anatomic model, such as distortions or errors that can occur through one or more of inadvertent placement of a catheter tip. Further, or instead, the rewind command can correct distortions or errors resulting from pressure of the catheter on tissue as the three-dimensional anatomic model is in a build phase.

Other aspects, features, and advantages will be apparent from the description and drawings, and from the claims.

BRIEF DESCRIPTION OF THE DRAWINGS

FIG. 5 is a schematic depiction of a projection of a three-dimensional data structure and a continuous surface of the anatomic structure projected to a graphical user interface of the ablation system of FIG. 1.

Like reference symbols in the various drawings indicate like elements.

DETAILED DESCRIPTION

The present disclosure is generally directed to devices, systems and methods of controlling the build of a three-dimensional model of a cardiac chamber of a patient. More specifically, a continuous surface displayed on a graphical user interface can be based on a three-dimensional data structure that can be modified to provide corresponding control over the displayed continuous surface. The three-dimensional data structure can include received catheter locations, and control over the displayed continuous surface can include a rewind command executed on the received catheter locations. The rewind command can be useful as a simple interface for undoing certain portions of a continuous surface displayed on a graphical user interface without requiring the use of a mouse to mark sections on a three-dimensional model displayed on a screen. Additionally, or alternatively, the simplicity of the rewind command can be useful for implementation as part of a remote control device in communication with a graphical user interface and operated by a physician (e.g., while the physician is manipulating the catheter).

It should be appreciated that, unless otherwise specified or made clear from the context, the systems and methods of the present disclosure can be used for any of various different medical procedures performed on an organ of a patient, in which direct visual access to the medical procedure is impractical and/or is improved by the use of a model of the anatomic structure. For the sake of clarity of explanation, however, the systems and methods of the present disclosure are described with respect to a cardiac chamber of a patient. Thus, for example, the systems and methods of the present disclosure can be used to facilitate visualization of a catheter inserted into a cardiac chamber as part of a medical treatment associated with diagnosis, treatment, or both of a cardiac condition (e.g., cardiac arrhythmia).

As used herein, the term "physician" shall be understood to include any type of medical personnel who may be performing or assisting a medical procedure and, thus, is inclusive of a doctor, a nurse, a medical technician, other similar personnel, and any combination thereof. Additionally, or alternatively, as used herein, the term "medical procedure" shall be understood to include any manner and form of diagnosis, treatment, or both, inclusive of any preparation activities associated with such diagnosis, treatment, or both. Thus, for example, the term "medical procedure" shall be understood to be inclusive of any manner and form of movement or positioning of a medical device in or relative to a cardiac chamber.

As used herein, the term "patient" should be considered to include any mammal, including a human, upon which a medical procedure is being performed.

Figure 1:
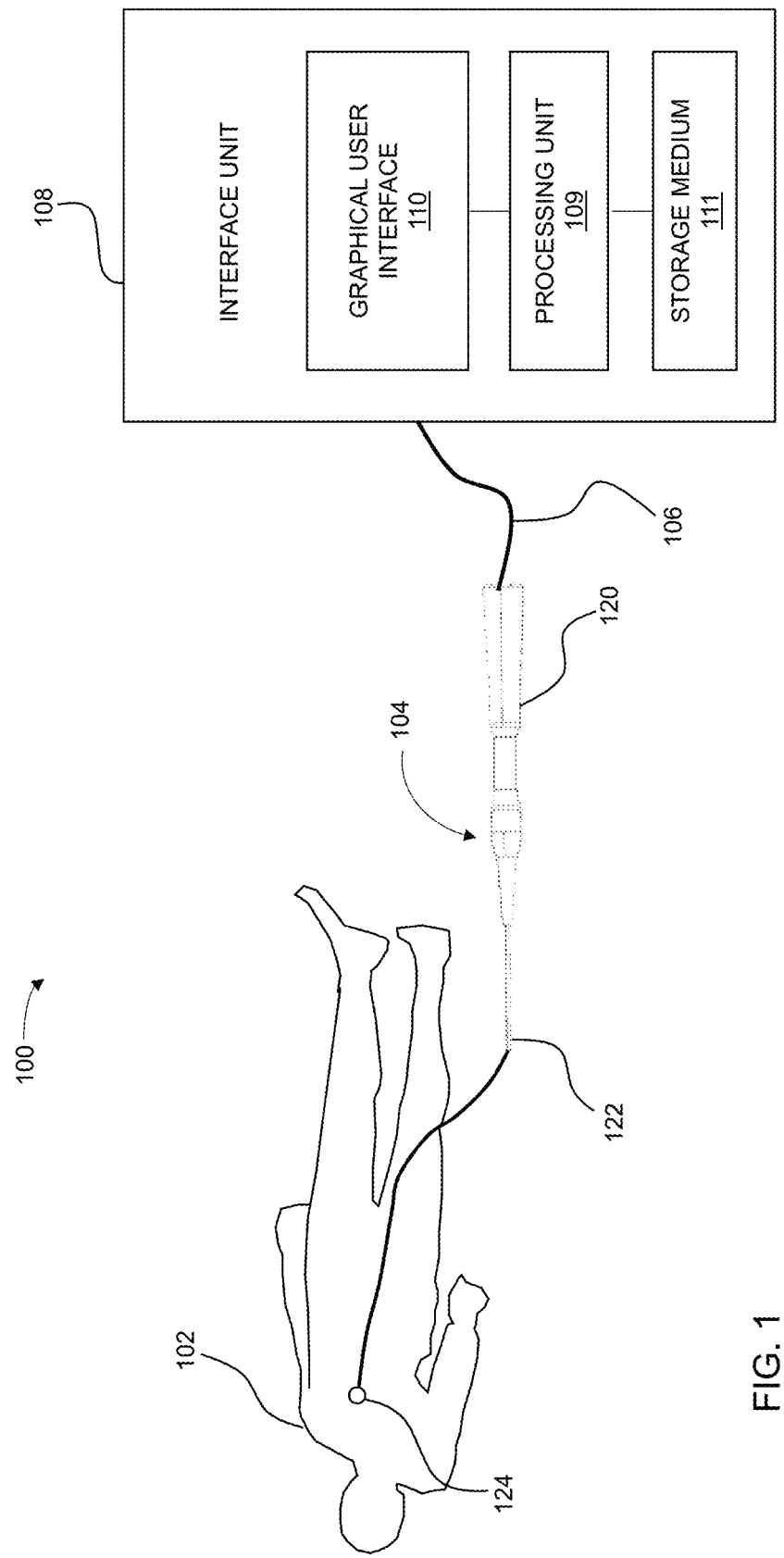
FIG. 1 is a schematic representation of a system during a medical procedure.

FIG. 1 is a schematic representation of a system 100 during a medical procedure performed in a cardiac chamber of a patient 102. The system 100 can include a catheter 104 connected, via an extension cable 106, to an interface unit 108. The interface unit 108 can include a processing unit 109 (e.g., one or more processors), a graphical user interface 110, and a storage medium 111. The graphical user interface 110 and the storage medium 111 can be in electrical communication (e.g., wired communication, wireless communication, or both) with the processing unit 109. The graphical user interface 110 can include a viewing window 138 (FIG. 5) on which, as described in greater detail below, a representation of the cardiac chamber can be displayed.

In use, the catheter 104 can be moved within the cardiac chamber (e.g., as part of a medical procedure), and the processing unit 109 can receive a plurality of location signals of the catheter 104 in the cardiac chamber during a build phase. The build phase can include, for example, a portion of a medical procedure in which a portion of the catheter 104 is moved within the cardiac cavity to gather spatial information related to the cardiac chamber. As described in greater detail below, the processing unit 109 can construct a data structure (e.g., a data structure including a three-dimensional data structure) including a representation of locations, within the cardiac chamber, visited by the catheter 104 during the build phase. As also described in greater detail below, the data structure can form a basis for a continuous surface representing a blood-tissue boundary in the cardiac chamber. The continuous surface can be displayed on the graphical user interface 110, representing at least a portion of a surface of the cardiac chamber.

As the catheter 104 is being moved within the cardiac chamber during the build phase, the catheter 104 can slip out of the cardiac chamber through a heart valve as the catheter 104 is moved through different locations to build the data structure. Such inadvertent positioning can result in errors in the continuous surface to be displayed on the graphical user interface 110.

To facilitate correcting errors that may occur during movement of the catheter 104 in the cardiac chamber during the build phase, the processing unit 109 can receive one or more rewind commands to modify the continuous surface on graphical user interface 110 according to any one or more of the methods described herein. As compared to deleting a portion of a three-dimensional data structure by marking it on a screen with a mouse, rewinding to modify the display of the continuous surface on the graphical user interface 110 can reduce the time associated with the procedure. Additionally, or alternatively, because the rewind command can facilitate editing a data structure upon which the continuous surface is based, the rewind command can result in a more accurate representation of the cardiac chamber on the graphical user interface 110 (e.g., as compared to an unedited representation of the cardiac chamber). This improvement in accuracy can be useful, for example, for using the representation of the cardiac chamber on the graphical user interface 110 to visualize a medical procedure performed on the cardiac chamber.

Figure 2:
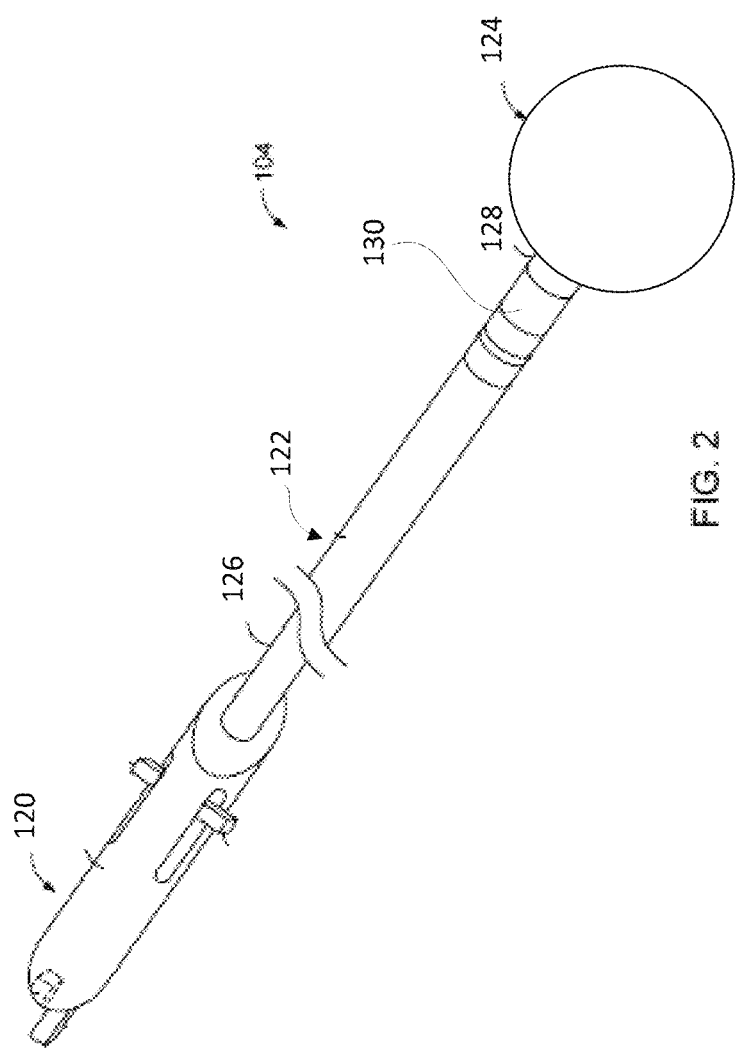
FIG. 2 is a perspective view of a catheter of the system of FIG. 1.
Figure 3:
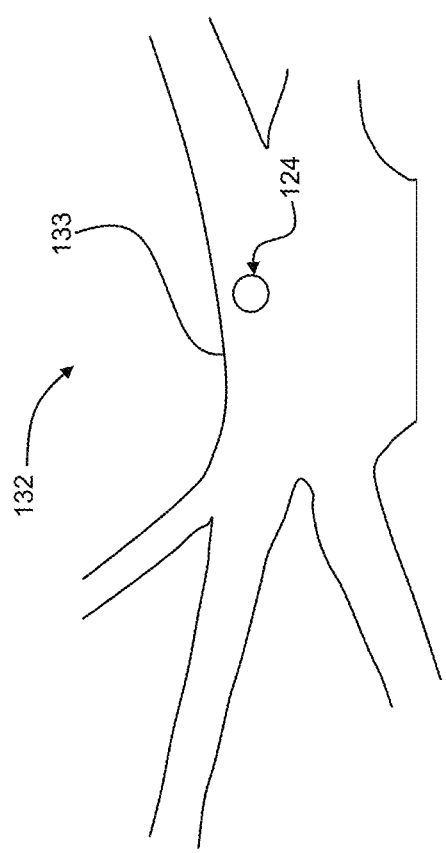
FIG. 3 is a schematic representation of a tip section of the catheter of FIG. 2 shown in a cardiac chamber.

Referring now to FIGS. 1-2, the catheter 104 can be any of various different catheters known in the art for insertion into a cardiac chamber for the purpose of diagnosis, treatment, or both. For example, the catheter can include a handle 120, a shaft 122, and a tip section 124. The shaft 122 can include a proximal portion 126 secured to the handle 120, and a distal portion 128 coupled to the tip section 124.

The tip section 124 can generally include any portion of the catheter 104 that directly or indirectly engages tissue in the cardiac chamber for the purpose of treatment, diagnosis, or both and, therefore, can include all manner and type of contact and/or non-contact interaction with tissue known in the art. For example, the tip section 124 can be used for contact interaction, non-contact interaction, or both with tissue in the form of energy interaction (e.g., electrical energy, ultrasound energy, light energy, and any combinations thereof) and/or chemical interaction with tissue in the cardiac chamber. Thus, by way of non-limiting example, the tip section 124 can deliver energy (e.g., electrical energy) to tissue in the cardiac chamber as part of any number of medical procedures.

In certain implementations, it can be desirable to deliver energy (e.g., RF energy) from the tip section 124 to targeted portions of cardiac tissue to ablate tissue at some depth relative to a surface of the cardiac chamber. Such ablations created by the tip section 124 along a surface of the cardiac chamber can, for example, treat cardiac arrhythmia in patients with this condition. However, the effectiveness of the ablations created using the tip section 124 in such a cardiac ablation procedure can be dependent upon location of the ablations. It should be appreciated, therefore, that accurate representation of the cardiac chamber on the graphical user interface 110 used to guide the tip section 124 can be advantageous for accurately delivering ablation energy to tissue in cardiac ablation procedures or other similar procedures in which there is a benefit derived from targeted energy delivery.

The catheter 104 can further, or instead, include a magnetic position sensor 130 along the distal portion 128 of the shaft 122. It should be appreciated that the magnetic position sensor 130 can be any of various magnetic position sensors well known in the art and can be positioned at any point along the distal portion 128. The magnetic position sensor 130 can, for example, include one or more coils that detect signals emanating from magnetic field generators. One or more coils for determining position with five or six degrees of freedom can be used.

The magnetic field detected by the magnetic position sensor 130 can be used to determine the position of the distal portion 128 of the catheter shaft 122 according to one or more methods commonly known in the art such as, for example, methods based on using a sensor, such as the magnetic position sensor 130, to sense magnetic fields indicative of the position of the magnetic position sensor 130 and using a look-up table to determine a location of the magnetic position sensor 130. Accordingly, because the tip section 124 is coupled to the distal portion 128 of the shaft 122 in a known, fixed relationship to the magnetic position sensor 130, the magnetic position sensor 130 also provides the location of the tip section 124.

While the location of the tip section 124 is described as being determined based on magnetic position sensing, electrical signal feedback, other position sensing methods, or combinations thereof can additionally or alternatively be used. For example, the location of the tip section 124 can be additionally, or alternatively, based on impedance, ultrasound, and/or imaging (e.g., real time MRI or fluoroscopy). Thus, more generally, the location of the tip section 124 at visited positions within the cardiac chamber can be based on one or more location signals generated based on one or more sensors carried on or near the tip section 124, sensors separate from the tip section 124, and combinations thereof.

Referring now to FIGS. 1-4, the tip section 124 of the catheter 104 can be moved in a cardiac chamber 132 (e.g., prior to application of an ablation treatment or other type of treatment). If the tip section 124 of the catheter 104 is movable in blood in the cardiac chamber 132 and obstructed only by a surface 133 of the cardiac chamber 132, the known positions of the tip section 124 of the catheter 104 can be taken together to provide an indication of the size and shape of a volume defined by the cardiac chamber 132 and can form a basis for a three-dimensional data structure corresponding to the volume defined by the cardiac chamber 132.

Figure 4:
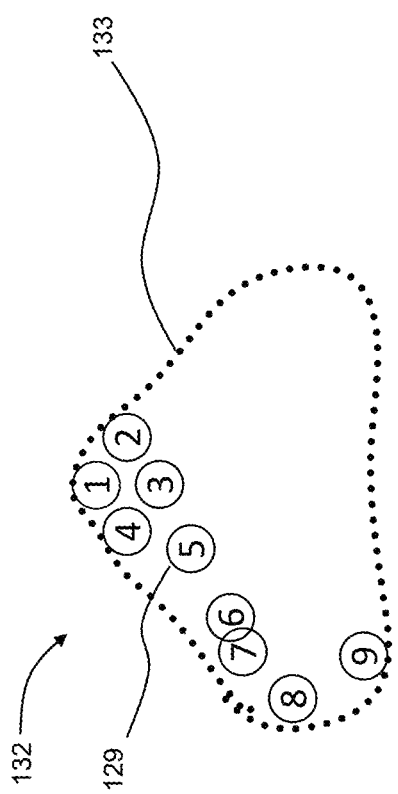
FIG. 4 is a schematic representation of visited locations of the catheter of FIG. 2 in the cardiac chamber of FIG. 3 during a medical procedure.
Figure 6A:
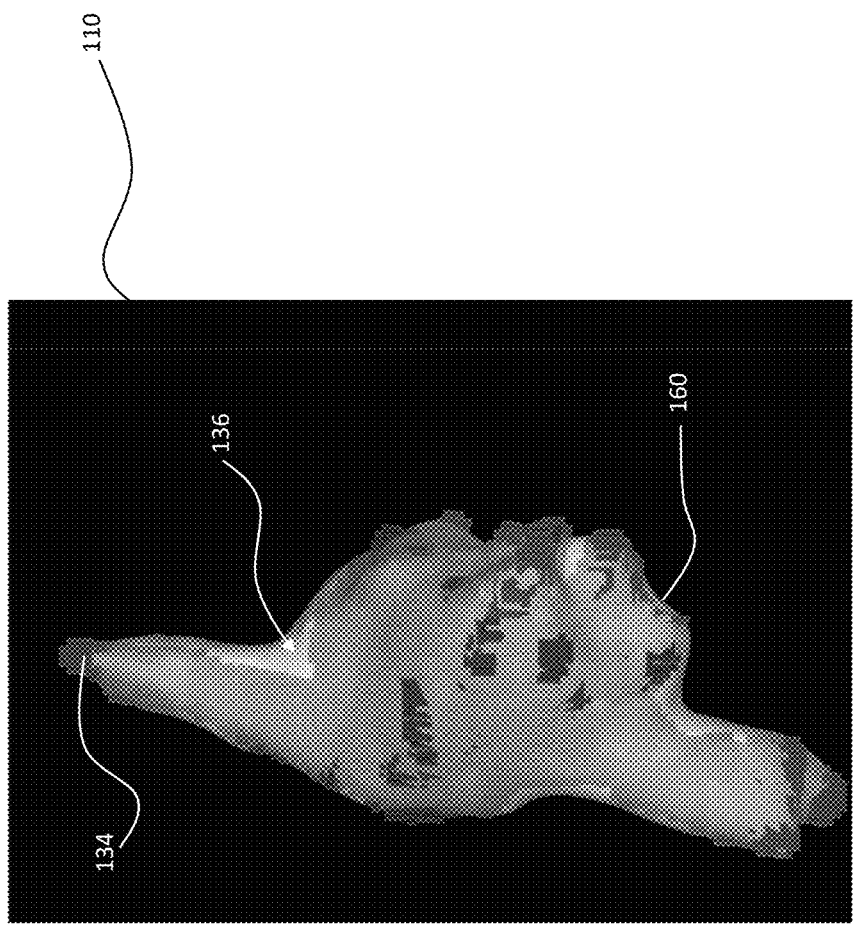
FIGS. 6A-6G is a time progression of the three-dimensional data structure and the continuous surface on the graphical user interface of the ablation system of FIG. 1 as a rewind function is applied.
Figure 6B:
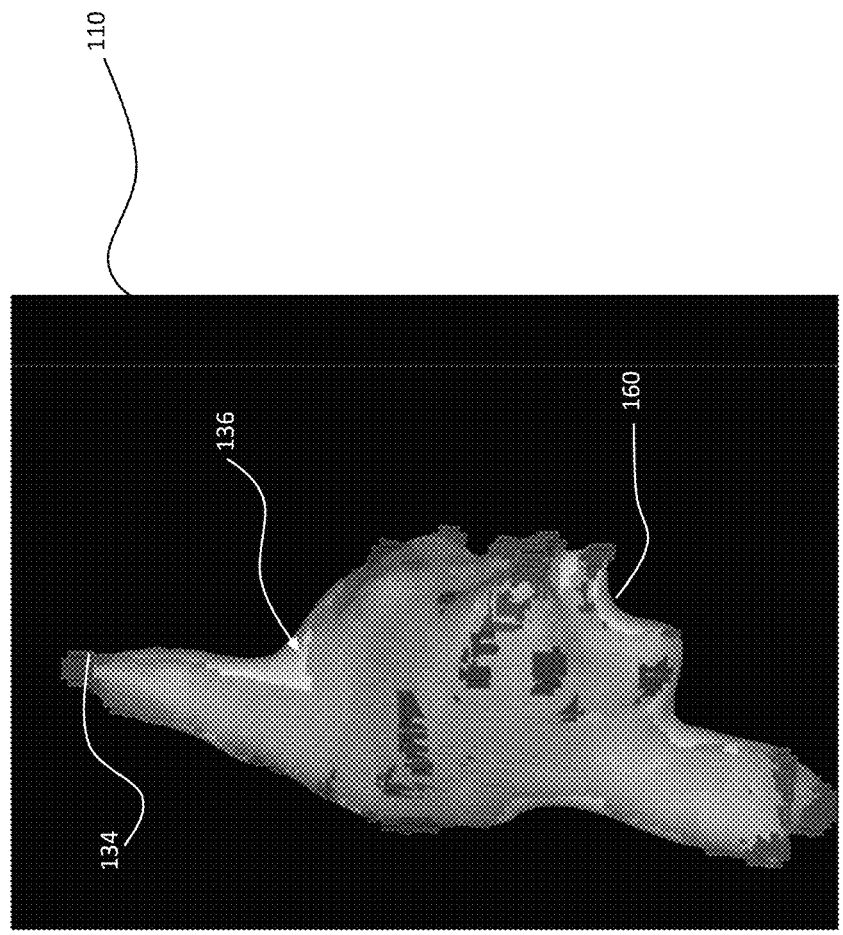
Figure 6C:
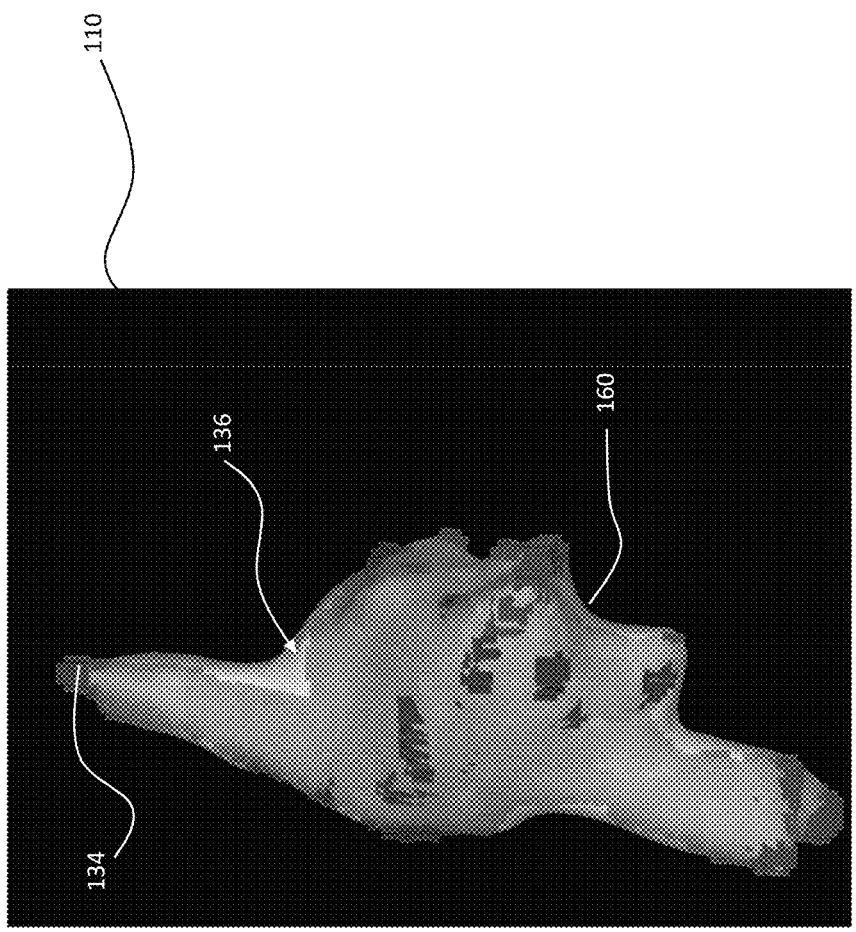
Figure 6D:
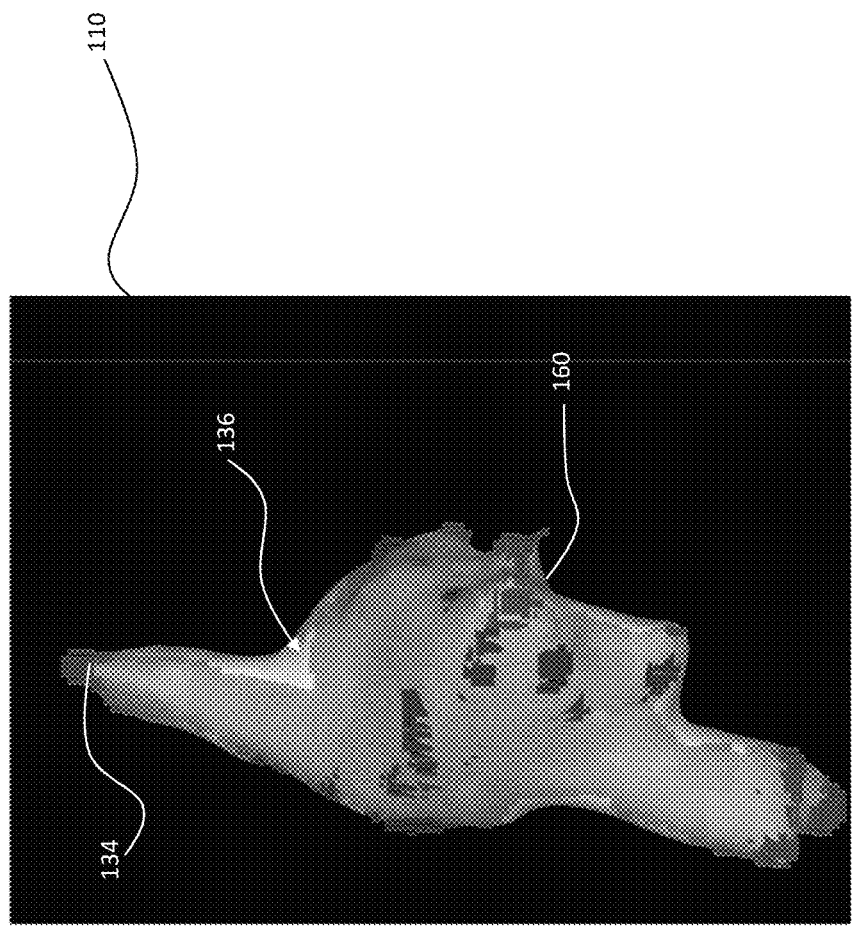
Figure 6E:
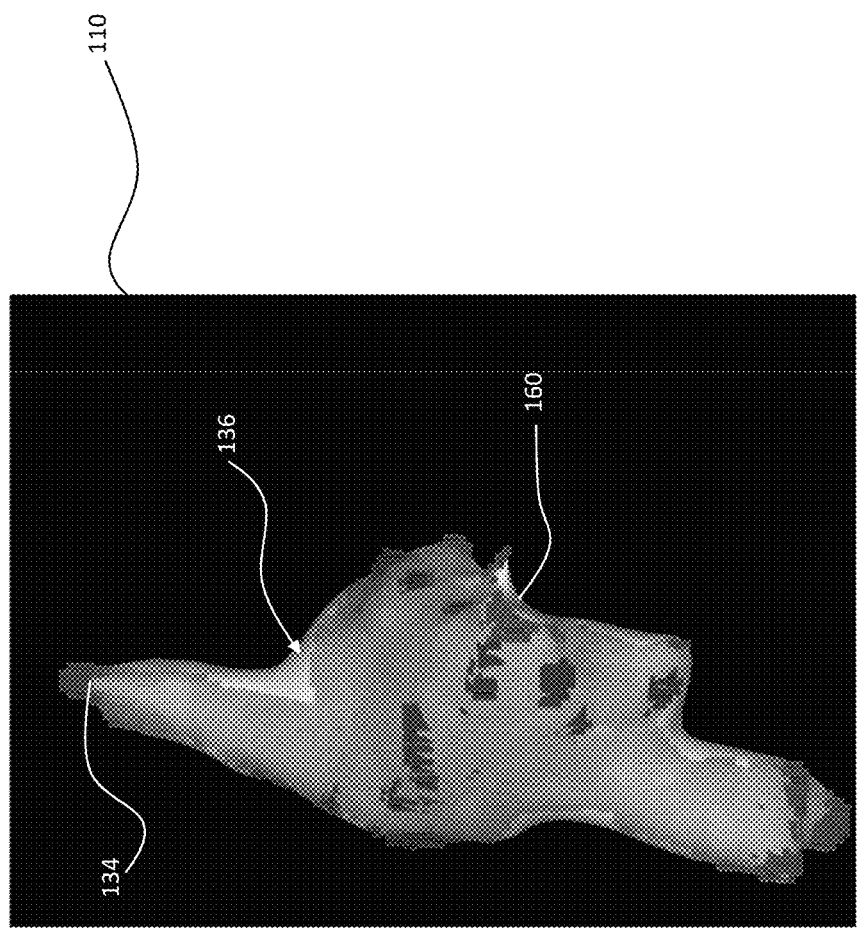
Figure 6F:
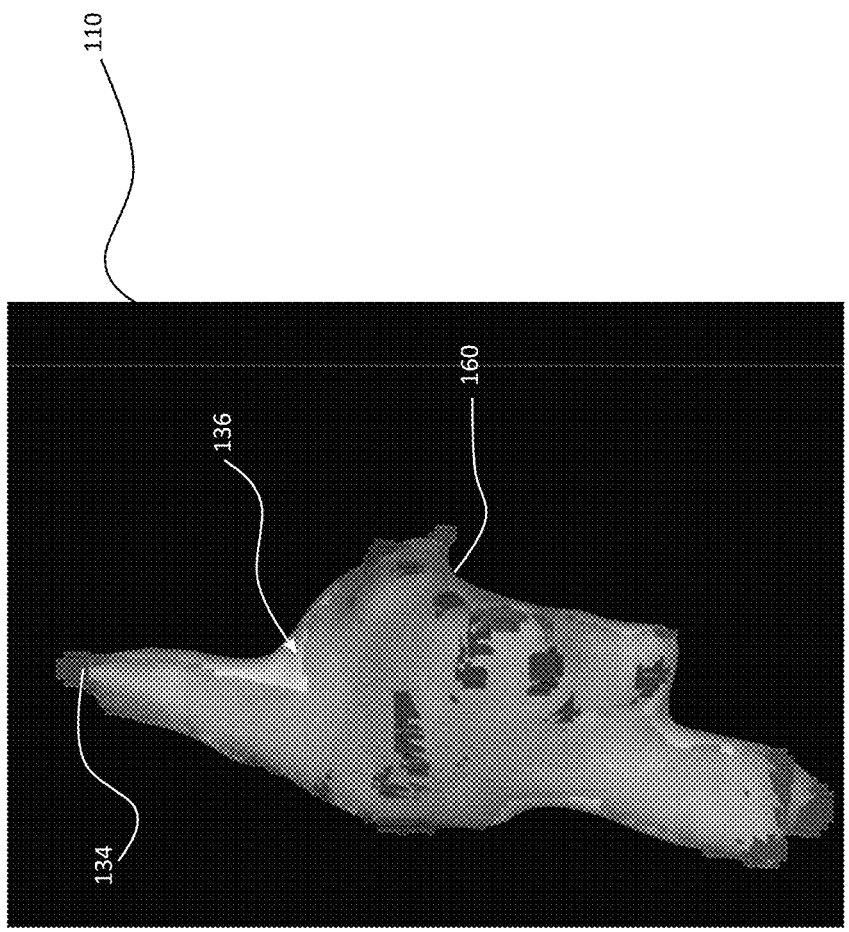
Figure 6G:
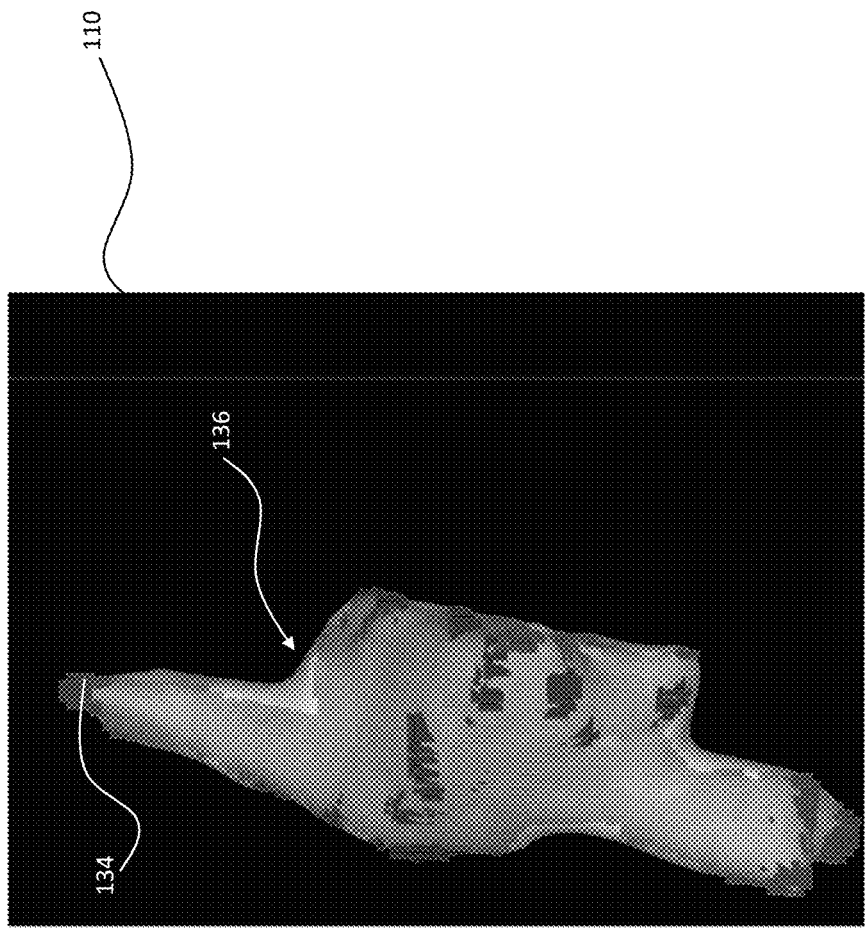

FIG. 4 is a schematic representation of locations 129 visited by the tip section 124 of the catheter 104 (FIGS. 2 and 3) in the cardiac chamber 132. Each location 129 can be associated with an indication of chronological order. In FIG. 4, for the sake of explanation, the indication of chronological order is shown as an ordered list of numbers (1 through 9), with each number indicated at one of the locations 129. In implementations, as described in greater detail below, it should be understood that the chronological order of the locations 129 or information derived from the chronological order can be stored in a corresponding portion of a data structure (e.g., a data structure including a three-dimensional data structure) based on the locations 129. Additionally, or alternatively, the chronological order of the locations 129 or information derived from such a chronological order can be represented in the arrangement of data in the data structure. For example, portions of the data structure corresponding to different periods of time (e.g., overlapping periods of time) can be stored in the storage medium 111 (FIG. 1) or at least accessible by the processing unit 109 (FIG. 1) based on chronological order.

The chronological ordering of the locations 129 can facilitate determination of the most recently visited locations 129 such that, for example, the most recently visited locations can be removed as part of an editing function. As used herein, an indication of chronological order can include an ordered sequence (e.g., a numbered list) arranged, for example, in ascending or descending order of most recently visited locations 129. Additionally, or alternatively, the indication of chronological order can include a time-stamp.

Each of the locations 129 can be visited by the tip section 124 (FIGS. 2 and 3) multiple times during the build phase. Accordingly, each location 129 can be associated with a corresponding number of indications of chronological order. For example, if a given one of the locations 129 is visited twice, that location can be associated with a corresponding number (i.e., two) of indications of chronological order. More generally, although the known position of the tip section 124 (FIGS. 2 and 3) can be in the location 129 multiple times, particular instances of such known positions can be tracked. As described in greater detail below, particular instances of known positions can be rewound as necessary as a continuous surface representing at least a portion of a surface of a cardiac chamber is being formed during the build phase. In general, rewinding to change the appearance of the continuous surface can be achieved through updating a display of a continuous surface from a first state to a second state, with at least a portion of the second state preceding at least a portion of the first state in the progressive formation of the continuous surface. In the description that follows, exemplary methods of updating the continuous surface can include accessing data in a three-dimensional data structure to change the appearance of the continuous surface on a display and, further or instead, accessing a data structure including multiple temporal states of the continuous surface to change the appearance of the continuous surface on the display.

FIG. 5 is a schematic representation of a three-dimensional data structure 134 and a continuous surface 136 projected onto the viewing window 138 of an image plane 140 of the graphical user interface 110 (FIG. 1). While the three-dimensional data structure 134 and the continuous surface 136 may both be projected onto the viewing window 138, it should be understood that the three-dimensional data structure 134 and the continuous surface 136 can be individually projected to the viewing window 138. For example, it may be desirable to project both the three-dimensional data structure 134 and the continuous surface 136 onto the viewing window 138 during the build phase to facilitate editing the three-dimensional data structure 134 and, thus, facilitate editing of the continuous surface 136 according to any one or more of the various different methods described herein. Additionally, or alternatively, it may be desirable to project only the continuous surface 136 (e.g., by making the three-dimensional data structure 134 at least partially translucent) onto the viewing window 138 while the catheter 104 (FIG. 3) is being used to diagnose and/or apply a treatment to a cardiac chamber (e.g., the cardiac chamber 132 in FIG. 3).

The three-dimensional data structure 134 can include, for example, a three-dimensional grid of voxels 135. Each voxel 135 can be a discrete element of volume corresponding to an analogous volume in the cardiac chamber. Together, the voxels 135 can form the three-dimensional data structure 134 which, in general, is a three-dimensional notational space. Thus, as a tip section of a catheter (e.g., the tip section 124 of the catheter 104 in FIGS. 2 and 3) visits a location in the cardiac chamber, the corresponding one of the voxels 135 can be flagged or otherwise indicated as "visited." Additionally, or alternatively, the chronological order in which the locations 129 were visited can be stored in the three-dimensional data structure 134. For example, each voxel 135 of the three-dimensional data structure indicated as "visited" can have one or more indications of chronological order associated with it. As another example, the three-dimensional data structure 134 can include a representation of a chronological ordering of the locations 129, and each voxel 135 of the three-dimensional data structure 134 can store an indication of the number of times the voxel 135 has been visited.

A rewind function can include removing, from the three-dimensional data structure 134, an indication of chronological order associated with a given one of the voxels 135. For example, if one of the voxels 135 corresponds to a location that has been visited twice by a tip section of a catheter (e.g., the tip section 124 of the catheter 104 in FIGS. 2 and 3), a rewind function can include removing the most recent indication of chronological order associated with the voxel 135 such that the earlier indication of chronological order associated with the voxel 135 remains stored in the three-dimensional data structure and the voxel 135 can remain flagged, or otherwise indicated as "visited." If the rewind function removes each of the indications of chronological order associated with the voxel 135, the voxel 135 can be changed from flagged to unflagged, or otherwise indicated as "not visited." For example, the voxel 135 in an unflagged state can be made to be translucent such that the voxel 135 is not visible on a graphical user interface (e.g., the graphical user interface 110 FIG. 1). As another example, a rewind function can include displaying on the graphical user interface 110 a portion of the three-dimensional data structure 134, or a representation derived from the three-dimensional data structure 134, corresponding to less than all of the available time periods. More specifically, a rewind function can include displaying on the graphical user interface 110 a portion of the three-dimensional data structure 134 corresponding to time periods not including the most recent locations 129.

A continuous surface 136 can be formed along a boundary of the three-dimensional data structure 134, with the continuous surface 136 representing at least a portion of a surface of the cardiac chamber 132. The continuous surface 136 can be extracted from the three-dimensional data structure 134 according to any one or more known computational algorithms for extracting a three-dimensional surface of an object. Examples of such algorithms include one or more of a "marching cubes" algorithm, a "ball-pivoting" algorithm, and a "power crust" algorithm.

Because the continuous surface 136 can be extracted from the voxels 135 of the three-dimensional data structure 134, it should be appreciated that rewinding to change the status of the voxels 135 of the three-dimensional data structure 134 can result in corresponding changes in the shape of the continuous surface 136. For example, in instances in which rewinding changes the status of one of the voxels 135 from "visited" to "unvisited," the resulting continuous surface 136 formed based on the voxels 135 in the three-dimensional data structure 134 may change in the vicinity of the voxel 135 that has been changed. Thus, a physician can use a rewind function to remove certain portions of the three-dimensional data structure 134 that were, for example, erroneously obtained and, in this way, can change the shape of the continuous surface 136. An exemplary change of this type is described in greater detail below.

The three-dimensional data structure 134 and the continuous surface 136 can be stored, for example, on the storage medium 111, along with instructions executable by the processing unit 109 to display the three-dimensional data structure 134, the continuous surface 136, or both, on the graphical user interface 110, as described in greater detail below. The instructions stored on the storage medium 111 and executable by the processing unit 109 to display one or both of the three-dimensional data structure 134 and the continuous surface 136 can be, for example, an application built using Visualization Toolkit, an open-source 3D computer graphics toolkit, available at www.vtk.org.

Referring now to FIGS. 1 and 5, the graphical user interface 110 can be two-dimensional such that the image plane 140 can correspond to a plane of the two-dimensional display of the graphical user interface 110, and the viewing window 138 can correspond to a field of view of the two-dimensional display of the graphical user interface 110. Accordingly, the image formed by projecting one or both of the three-dimensional data structure 134 and the continuous surface 136 onto the viewing window 138 can be displayed on the graphical user interface 110. As described in greater detail below, a physician can, in certain instances, interact with the projection of the three-dimensional data structure 134, the continuous surface 136, or both on the graphical user interface 110 to remove specific portions of the three-dimensional data structure 134.

FIGS. 6A-6G are, collectively, a depiction of a time progression of an example of a rewind editing function applied to the three-dimensional data structure 134 projected onto the graphical user interface 110. In each of FIGS. 6A-6G, the continuous surface 136 formed on the three-dimensional data structure 134 is also shown and, for the sake of clarity, only a single view is shown. It should be appreciated, however, that multiple views of the three-dimensional data structure 134, the continuous surface 136, or both can be displayed on the graphical user interface 110 as the rewind editing function is applied to the three-dimensional data structure 134. In such instances, multiple views can be useful for providing a physician with additional details regarding the three-dimensional data structure 134, which can guide the physician in determining how far to rewind the visited locations in the cardiac chamber.

In the time progression of the exemplary rewind editing function shown in FIGS. 6A-6G, rewinding can change the appearance of the voxels 135 in a chronological order (e.g., in a reverse order of when the voxel 135 was visited). Through such changes in the appearance of the voxels 135, a modified portion 160 of the continuous surface 136 appears to move over the course of the time progression. For example, in the time progression shown in FIGS. 6A-6G, the modified portion 160 moves as the rewind function appears to delete or otherwise change the appearance of voxels 135 associated with a particular time window in the build phase of the three-dimensional data structure 134. Comparing FIG. 6A to FIG. 6G, it should be appreciated that the rewind function accesses data in the three-dimensional data structure 134 to change the appearance of the associated continuous surface 136.

While the rewind function shown in FIGS. 6A-6G has been described with respect to a three-dimensional data structure including voxels, it should be appreciated that other implementations are additionally or alternatively possible. For example, it should be appreciated that the three-dimensional data structure 134 can include one or more of zero-dimensional elements (e.g., points), one-dimensional elements (e.g., edges and/or contours), two-dimensional elements (e.g., surfaces and/or meshes), and four-dimensional elements (e.g., tesseracts). Further, or instead, portions of the three-dimensional data structure 134 can correspond to different periods of time (e.g. overlapping periods of time), and the portions can be accessible based on chronological order. Thus, by way of a specific non-limiting example, the three-dimensional data structure 134 can include surface elements corresponding to different time periods, and rewinding can include accessing those surface elements corresponding to time periods not including the most recent locations 129 (FIG. 4) to form a basis for displaying a rewound state of the continuous surface 136. For the sake of clarity of illustration, the rewind function shown in FIGS. 6A-6G has been described with respect to accessing portions a three-dimensional data structure. More generally, however, it should be appreciated that rewinding the continuous surface 136 can include additionally, or alternatively, accessing other types of data structures. For example, a data structure can include consecutive temporal states of the continuous surface 136. Continuing with this example, a rewind function can include selecting the temporal state of the continuous surface 136 corresponding to the time selected by rewinding. Because the consecutive temporal states of the continuous surface 136 are stored in the data structure, such implementations can reduce the computational requirements and/or time delay associated with editing the continuous surface 136, as compared to implementations requiring regeneration of the displayed surface following an editing command.

In certain instances, the consecutive temporal states of the continuous surface 136 can be distinguished from one another by a respective key frame based on a change in the continuous surface as the continuous surface is progressively formed through movement of the catheter in the cardiac chamber of the patient. As used herein, a key frame shall be understood to correspond to a temporal state of the continuous surface 136 after a significant change from a preceding temporal state of the continuous surface 136. Thus, for example, the continuous surface 136 corresponding to each temporal state can define a respective volume, and each key frame can correspond substantially (e.g., ±25 percent) to a predetermined change (e.g., about 1 $cm^3$) in volume between respective consecutive temporal states of the continuous surface.

The computer executable instructions stored on the storage medium 111 (FIG. 1) can cause the processing unit 109 (FIG. 1) to modify the three-dimensional data structure 134 according to one or more of the following exemplary methods. Unless otherwise indicated, each of the following exemplary methods can be implemented using the system 100 (FIG. 1) and/or one or more components thereof.

Figure 7:
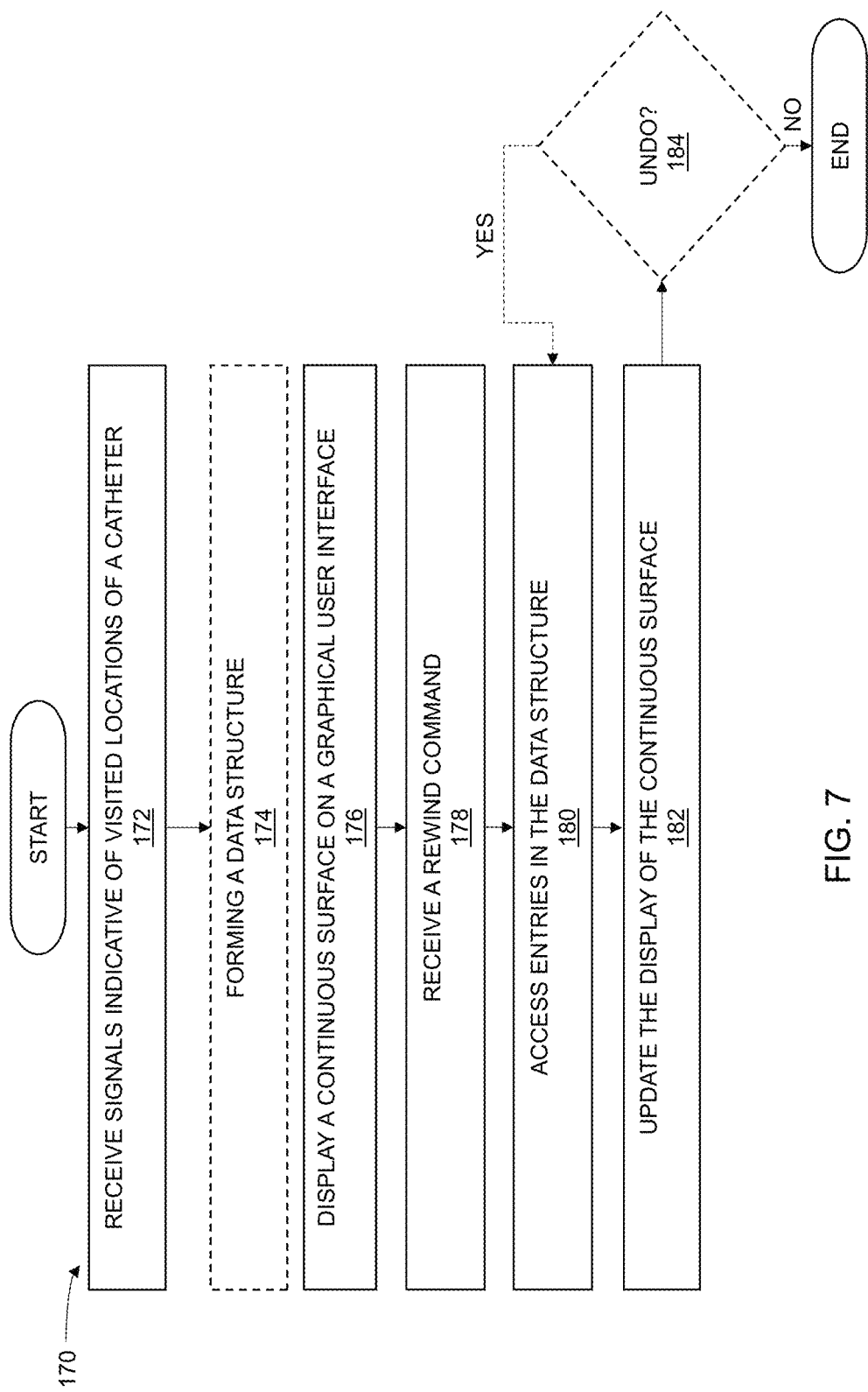
FIG. 7 is a flow chart of an exemplary method of updating a display of a continuous surface displayed on a graphical user interface based on a rewind command.

FIG. 7 is a flowchart of an exemplary method 170 of updating a display of a continuous surface on a graphical user interface based on a rewind command. The exemplary method 170 can include receiving 172 a plurality of signals indicative of respective visited locations of a catheter in a cardiac chamber of a patient, displaying 176 (on a graphical user interface) a continuous surface (representing at least a portion of a surface of the cardiac chamber) derived from a data structure and based on the received catheter locations, receiving 178 a rewind command (e.g., from an input device), accessing 180 one or more entries in the data structure, and updating 182 the display of the continuous surface on the graphical user interface. As described in greater detail below, accessing 180 the one or more entries in the data structure can be based on the received 178 rewind command and on the order of receipt of the received 172 locations of the catheter. As also described in greater detail below, updating 182 the display of the continuous surface on the graphical user interface can be based on the accessed 180 one or more entries in the data structure such that, in general, the display of the continuous surface on the graphical user interface can change in response to the rewind command.

In general, receiving 172 the plurality of signals indicative of respective visited locations of the catheter in the cardiac chamber of the patient can include receiving signals indicative of the location of the catheter according to any one or more of the methods described herein. As used herein, the received 172 plurality of location signals of the catheter generally corresponds to locations visited by a tip section of the catheter (e.g., the tip section 124 of the catheter 104 of FIG. 2) in the cardiac chamber. More generally, however, it should be understood that the plurality of location signals of the catheter can correspond to locations visited by any portion of the catheter that can be sensed or otherwise determined in the cardiac chamber and, thus, can include signals from one or more sensors disposed along the catheter (e.g., the sensor 125 in FIG. 2). The received 172 plurality of signals can be, for example, a plurality of signals received from a single sensor over a period of time. For example, the received 172 plurality of signals can be one or more signals from a magnetic position sensor (such as the magnetic position sensor 130 described above with respect to FIG. 2). Additionally, or alternatively, the received 172 plurality of signals can be a plurality of signals received from multiple, different types of sensors that individually, or in combination, provide information regarding the location of the catheter in the cardiac chamber.

Displaying 176 the continuous surface representing at least a portion of the surface of the cardiac chamber can include projecting the continuous surface onto a display of a graphical user interface as described, for example, with respect to FIG. 5. While displaying 176 the continuous surface has been described as being on a two-dimensional display, it should be appreciated that displaying 176 the continuous surface can additionally, or alternatively, include projecting a three-dimensional image of the continuous surface. For example, displaying 176 the continuous surface can include projecting a three-dimensional image of the continuous surface as part of one or more of a virtual reality environment and an augmented reality environment.

In general, as the catheter is moved in the cardiac chamber during the build phase, the displayed 176 continuous surface can undergo corresponding changes based on the received 172 signals indicative of visited locations of the catheter. Thus, for example, a physician can view the displayed 176 continuous surface and make a determination regarding whether or not rewinding or other editing would improve the displayed 176 continuous surface. Displaying 176 the continuous surface can, in certain instances, further include displaying one or more portions of the data structure, which can provide the physician with more specific information regarding the visited locations than may be apparent from the display of the continuous surface alone.

In general, receiving 178 the rewind command can include receiving a signal from any one or more of various different input devices. Examples of input devices that can send the rewind command include one or more of a mouse, a keyboard, a microphone, a touchscreen, and a capacitive touch sensor. Additionally, or alternatively, it should be appreciated that a physician may communicate (e.g., verbally communicate) a rewind command from within the sterile field to an operator outside of the sterile field. The rewind command can be received 178 directly or indirectly at a processing unit (e.g., the processing unit 109 in FIG. 1). As an example, the rewind command can be received 178 by the processing unit directly from a physician, or other medical personnel, in a sterile field. As a more specific example, the rewind command can be received 178 from a button on a remote control operated by the physician in the sterile field. As yet a more specific example, the button on the remote control can be integrated into the handle of the catheter or rotatably coupled to the catheter such that the physician can send the rewind command while manipulating the catheter during a medical procedure.

In general, a rewind command can create a visual impression of reversing at least a portion of the construction of the continuous surface on a graphical user interface. Thus, a rewind command can include any command that initiates or otherwise results in modification of a visual representation of at least a portion of the continuous surface displayed 176 on the graphical user interface. The modification can be based at least in part upon a chronological order of visited locations of a catheter. For example, a rewind command can include deleting, deselecting, or not accessing a portion of the data structure such that an earlier state of the continuous surface is displayed on the graphical user interface. Additionally, or alternatively, a rewind command can include turning portions of the data structure, such as a three-dimensional data structure, from visible to translucent (e.g., to provide an appearance of at least a portion of the three-dimensional data structure being deleted) on a graphical user interface based on a chronological order in which locations in the cardiac chamber were visited by the catheter.

Receiving 178 the rewind command can include, for example, receiving a signal indicative of a quantity of discrete inputs (e.g., a quantity of clicks from a click-based input device). In such instances, the number of the discrete inputs can be proportional to a time period or chronological sequence length corresponding to the one or more accessed 180 entries of the data structure. For example, receiving 178 the rewind command including a signal indicative of three discrete inputs can correspond to removal of the one or more indications of chronological order corresponding to the last three visited locations of the catheter in the cardiac chamber. A continuous surface formed based on the data structure with the removed indications of chronological order can correspond to an earlier state of the continuous surface. Additionally, or alternatively, each discrete input can correspond to a predetermined period of time. As a specific example, each discrete input can correspond to a predetermined period of time (e.g., five seconds) such that receiving 178 the rewind command including three discrete inputs can correspond to returning to a previous state of the continuous surface corresponding to a time that is three predetermined periods of time earlier (e.g., fifteen seconds earlier in the case in which each predetermined period of time is five seconds). It should be appreciated that the proportionality between the quantity of the discrete inputs and the change in state of the continuous surface to be displayed can be selectable (e.g., by the physician) to facilitate, for example, making both fine and coarse adjustments to the continuous surface during a build phase. Further, or instead, the duration of each discrete input can be proportional to a duration of a time sequence to be rewound from the continuous surface. Continuing with this example, the physician can press an input longer to further rewind the continuous surface during the build phase. As another example, the quantity of discrete inputs can correspond to a predetermined change in volume defined by the continuous surface. Continuing with this example, each discrete input can correspond to rewinding a predetermined volume (e.g. about 1 $cm^3$) such that receiving 178 the rewind command including three discrete inputs can correspond to reducing the volume defined by the continuous surface by at least three times the predetermined volume (e.g. about 3 $cm^3$ in the case in which the predetermined volume is about 1 $cm^3$).

Receiving 178 the rewind command can include displaying, on the graphical user interface, visual indicia of the received rewind command. For example, the graphical user interface can display an icon indicating that the rewind command has been received 178. As a further or alternative example, displaying visual indicia on the graphical user interface can include displaying a spatial extent of the received 178 rewind command. As used here, the spatial extent of the received 178 rewind command should be understood to include a difference between a current state of the continuous surface and the state of the continuous surface resulting from application of the received 178 rewind command.

In general, displaying visual indicia of the received rewind command can be useful for providing feedback to a physician or other user and, thus, can reduce the likelihood that the physician or other user will inadvertently provide more rewind commands than intended. In certain implementations, receiving 178 the rewind command can include displaying the visual indicia of the rewind command on one or more of the data structure and the continuous surface. Additionally, or alternatively, the visual indicia of the rewind command can be displayed as a surface or volume separate from the continuous surface and the data structure. The visual indicia can provide a preview of the state of the continuous surface resulting from application of the received 178 rewind command. For example, a spatial extent of the received 178 rewind command can be highlighted or otherwise distinguished from other portions of the continuous surface to provide the physician or other user with a visual indication of a pending rewind command. In such instances, the continuous surface can be modified along the spatial extent of the received 178 rewind command upon receipt, for example, of a subsequent input to confirm removal.

As a further or alternative example, displaying the visual indicia on the graphical user interface can include displaying a temporal extent of the received rewind command, with the temporal extent corresponding to a time between the first state of the continuous surface and the second state of the continuous surface. The temporal extent of the rewind command can be useful for providing the physician or another user with an indication of how far back a display of the continuous display is rewound. Additionally, or alternatively, the temporal extent of the rewind command can be useful for providing the physician or another user with an indication of how far forward a display of the continuous display can be undone, as described in greater detail below.

In general, accessing 180 the one or more entries of the data structure can be based on the received 178 rewind command and on an order of receipt of the received 172 locations of the catheter. Accessing 180 the one or more entries of the data structure can include modifying the one or more entries that correspond to the received locations of the catheter. For example, in implementations in which the data structure includes a three-dimensional data structure, as voxels of the three-dimensional data structure are being flagged based on received locations of the catheter, accessing 180 the one or more entries of the data structure can include modifying only those voxels that have been flagged and, thus, correspond to locations visited by the catheter. Accordingly, in this way, accessing 180 the one or more entries of the data structure can include modifying entries of a three-dimensional data structure corresponding to inadvertent placement of the catheter (e.g., in the event of catheter movement through a valve and out of the cardiac chamber).

Accessing 180 the one or more entries in the data structure can include, for example, removing the one or more entries from the data structure. For example, removing the one or more entries from the data structure can include removing only those entries in the data structure that are not represented by earlier data in the chronological sequence of locations visited by the catheter after modifying those entries associated by the rewind command. As used herein, removal of an entry from the three-dimensional data structure can include unflagging the entry as corresponding to a visited location of the catheter. Accessing 180 the one or more entries in the data structure can, in some cases, result in only removal of indications of chronological order of locations while the flags remain unchanged. An entry that is unflagged can be omitted from consideration in a surface generation algorithm used to generate the continuous surface from the data structure (e.g., from a three-dimensional data structure). Additionally, or alternatively, removing the one or more entries in the data structure can include adjusting the one or more entries to be translucent such that the one or more entries are not shown on the graphical user interface.

In certain implementations, accessing 180 the one or more entries of the data structure can be based on a reverse chronological order of receipt of the corresponding received locations of the catheter. For example, accessing 180 the one or more entries of the data structure can include modifying the one or more entries based on a last-in-first-out priority. It should be appreciated, however, that other orders of modification are additionally, or alternatively, possible. For example, accessing 180 the one or more entries of the data structure can include accessing those entries of the data structure corresponding to time periods not including the most recent locations visited by the catheter. Additionally, or alternatively, accessing 180 the one or more entries can be based on all of the entries of the three-dimensional data structure corresponding to a predetermined period. As a specific example, accessing 180 the one or more entries can include removing indications of chronological order corresponding to the most recently received location or locations of the catheter within a predetermined period, such as a predetermined period immediately preceding receipt 178 of the rewind command.

In general, updating 182 the display of the continuous surface on the graphical user interface can be based on the accessed 180 one more entries in the data structure and can include changing the appearance of the continuous surface on the graphical user interface. Additionally, or alternatively, updating 182 the display of the continuous surface can include reforming at least a portion of the continuous surface based on the accessed 180 one or more entries of the data structure. For example, updating 182 the display of the continuous surface can include reapplying one or more surface generation algorithms to the data structure to reform at least a portion of the continuous surface. Additionally, or alternatively, updating 182 the display of the continuous surface can be based on changing pointers in the data structure to point to, for example, an earlier state of the continuous surface stored in the data structure, as described in greater detail below. In certain instances, updating 182 the display of the continuous surface can occur after each portion of the three-dimensional surface representation is accessed 180 such that the updating 182 of the display of the continuous surface can appear to occur on the graphical user interface substantially in real time. In some instances, updating 182 the display of the continuous surface representation can occur based on a user input (e.g., a refresh command).

The method 170 can, optionally, include forming 174 the data structure. Forming 174 the data structure can additionally, or alternatively, include associating each visited location with a chronological order in the data structure. Such chronological ordering can include any one or more of the various different techniques of chronological ordering described herein. Thus, for example, multiple visits by the catheter to a given location in the cardiac chamber can be tracked in the data structure as unique instances of visiting the location according to any one or more of the various different methods described herein.

In certain implementations, the data structure can be formed 174 as a three-dimensional data structure based on the received locations of the catheter in the cardiac chamber. For example, the three-dimensional data structure can include a three-dimensional grid. Voxels in the three-dimensional grid can correspond, in certain instances, to locations in a three-dimensional coordinate system and, thus, can be used to track locations visited by the catheter in the cardiac chamber.

In some implementations, forming 174 the data structure can include, for example, storing portions of the continuous surface representing different but optionally overlapping periods of time such that the portions are accessible or selectable based on chronological order. As a more specific example, forming 174 the data structure can include storing a sequence of continuous surfaces accessible based on chronological order, as described in greater detail below.

The exemplary method 170 can optionally include receiving 184 an undo command. Based on the undo command, the display of the continuous surface on the graphical user interface can be modified to a third state of the continuous surface, with the third state of the continuous surface following the second state of the continuous surface in the progressive formation of the continuous surface. For example, the third state of the continuous surface can precede or, in some instances, can be substantially contemporaneous with the first state of the continuous surface in the progressive formation of the surface. Accordingly, on the graphical user interface, the undo command can appear to revert modifications to portions of the continuous surface and/or the data structure that were previously modified by a previously received rewind command. Thus, in general, a physician or other user can control the display of the continuous surface on the graphical user interface through a combination of the undo command and the rewind command to navigate forward and backward in a time sequence of a plurality (sometimes known as a stack) of states of the continuous surface. In some instances, continuing to progressively form the continuous surface following application of the undo command or the rewind command can interrupt the ability to toggle between the undo command and the rewind command.

Receiving 184 the undo command can include, for example, receiving a signal indicative of a quantity of discrete inputs. Continuing with this example, the state of the continuous surface preceding the update of the display of the continuous surface can be based on the quantity of discrete inputs.

In certain implementations, the undo command can be symmetric with the rewind command. For example, in instances in which a discrete input corresponds to a rewind increment of 5 seconds of catheter locations, a discrete input of an undo command can correspond to restoring 5 seconds of catheter locations. In some implementations, however, the undo command and the rewind command can be asymmetric. For example, the undo command and the rewind commands can be asymmetric with respect to one another such that restoring can be done at a faster rate than rewinding. It should be appreciated that in some instances, the relative symmetry between the rewind command and the undo command can be adjustable (e.g., according to a preference of a physician or other user).

Receiving 184 the undo command can include receiving one or more signals from an input device, including any one or more of the input devices described herein. Thus, for example, the same input device that sends the rewind command can send the undo command.

Figure 8:
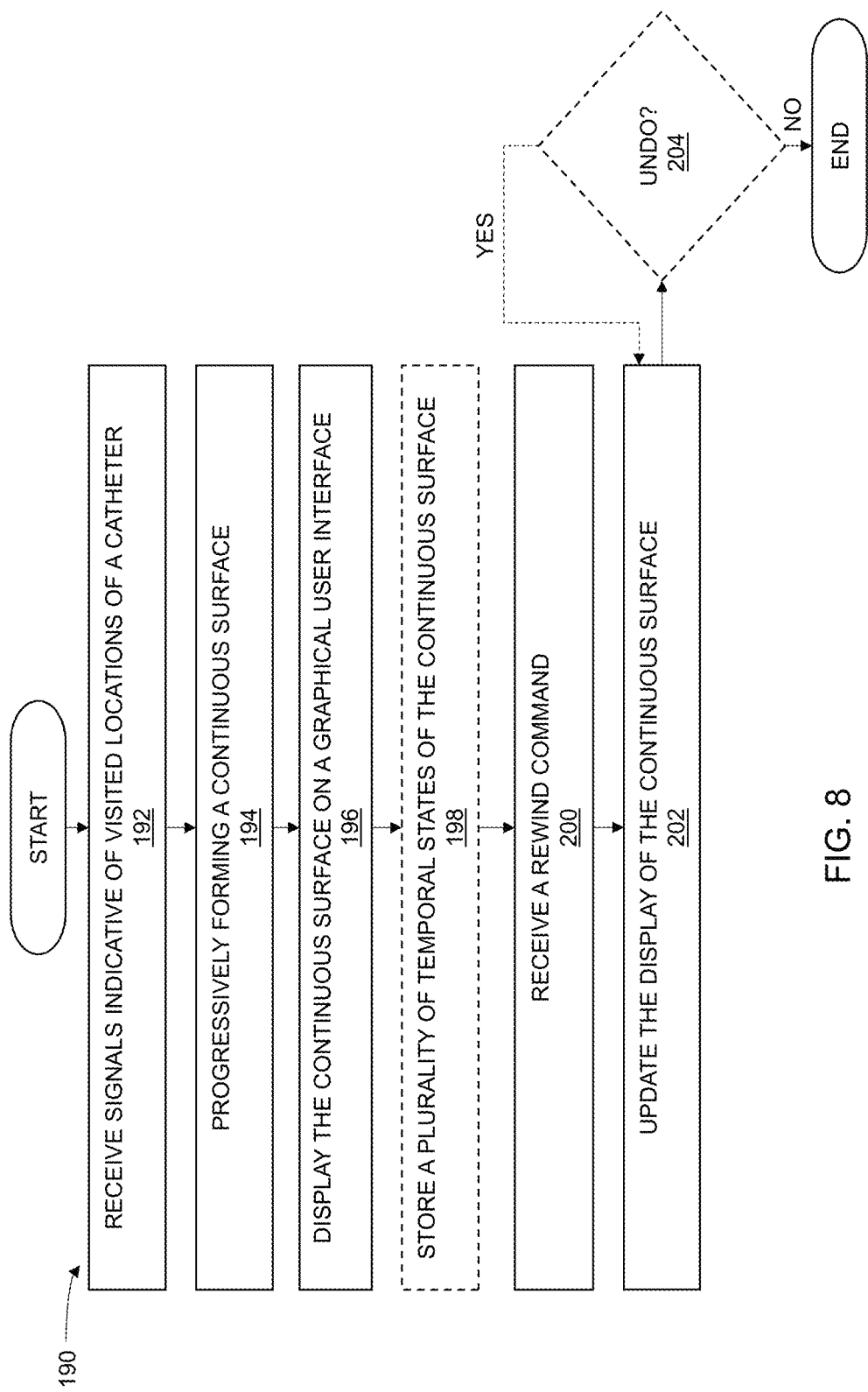
FIG. 8 is a flow chart of an exemplary method of updating a display of a continuous surface displayed on a graphical user interface based on a rewind command.

FIG. 8 is a flowchart of an exemplary method 190 of modifying a data structure based on a rewind command. The exemplary method can include receiving 192 a plurality of signals indicative of respective visited locations of a catheter in a chamber of a patient, progressively forming 194 a continuous surface representing at least a portion of a surface of the cardiac chamber based on the visited locations of the catheter, receiving 200 a rewind command from an input device, and, based on the received 200 rewind command, updating 202 a display of a continuous surface on the graphical user interface from a first state of the continuous surface to a second state of the continuous surface. At least a portion of the second state can precede at least a portion of the first state in the progressive formation of the continuous surface such that updating 202 the display of the continuous surface on the graphical user interface results in rewinding the display of the continuous surface. In general, it should be appreciated that one or more portions of the exemplary method 190 can be implemented in combination with or as an alternative to one or more portions of the exemplary method 170 (FIG. 7), unless otherwise indicated or made clear from the context.

Receiving 192 the signals indicative of the respective visited locations of the catheter can include any one or more of the methods of receiving signals described herein. For example, unless otherwise indicated or made clear from the context, receiving 192 the signals indicative of the visited locations of the catheter should be understood to be analogous to receiving 172 the signals as described with respect to the exemplary method 170 described with respect to FIG. 7.

Progressively forming 194 a continuous surface can include forming the continuous surface based on a chronological order of the visited locations of the catheter in the cardiac chamber. For example, progressively forming 194 a surface based on the visited locations of the catheter can include applying a surface generation algorithm to a data structure (e.g., three-dimensional data structure) including the visited locations. The surface generation can be any one or more of various different surface generation algorithms known in the art. As the catheter is moved in the cardiac chamber and additional visited locations are received, progressively forming 194 the continuous surface can include forming new instances of the continuous surface based on the additional visited locations. Each instance of the continuous surface is referred to herein as a "state."

Displaying 196 the continuous surface on the graphical user interface can include displaying a state of the continuous surface. The displayed 196 state of the continuous surface can generally correspond to a most recent state of the continuous surface such that the physician can have a substantially real-time indication of progress of the build phase. In general, unless otherwise indicated or made clear from the context, displaying 196 the continuous surface on the graphical user interface should be understood to be analogous to displaying 176 a continuous surface on a graphical user interface as described with respect to the exemplary method 170 corresponding to FIG. 7.

Receiving 200 the rewind command can include any of the various different methods of receiving a rewind command described herein. Thus, for example, receiving 200 the rewind command can be analogous to receiving 178 the rewind command, as described with respect to the exemplary method 170 corresponding to FIG. 7. As a more specific example, receiving 200 the rewind command can include receiving a signal indicative of a quantity of discrete inputs as described with respect to the exemplary method 170 corresponding to FIG. 7.

In general, updating 202 the display of the continuous surface from the first state to the second state provides a visual impression of rewinding the continuous surface to a previous state in the progressive formation 194 of the continuous surface. It should be understood, however, that the second state of the continuous surface need not have been previously displayed on the graphical user interface prior to updating 202 the display of the continuous surface.

That is, in certain implementations, the second state can be similar, but not necessarily identical, to an earlier state of the continuous surface displayed 196 on the graphical user interface.

Following updating 202, the progressive formation 194 can be continued from the second state of the continuous surface such that the first state of the continuous surface is effectively removed from the display on the graphical user interface. Once removed from the display on the graphical user interface, it should be appreciated that the first state can be stored in a data structure (e.g., for retrieval in implementations including an undo command) or removed entirely from a data structure.

Updating 202 the continuous surface can be based on volumetric differences associated with states of the continuous surface as the continuous surface is progressively formed 194. That is, in each state, the continuous surface can include a closed shape defining a volume in a three-dimensional representation of the cardiac chamber. As the continuous surface is progressively formed 194, the volume associated with each state of formation of the continuous surface can stay the same or increase. For example, the first state of the continuous surface can define a first volume and the second state of the of the continuous surface can define a second volume, different from the first volume. More specifically, because the second state precedes the first state in the progressive formation 194 of the continuous surface, the second volume can be less than the first volume. Thus, updating 202 the display of the continuous surface on the graphical user interface from the first state of the continuous surface to the second state of the continuous surface can produce the visual impression of rewinding the continuous surface.

In implementations in which the received 200 rewind command includes a signal indicative of a quantity of discrete inputs, the difference between the first volume defined by the first state of the continuous surface and the second volume defined by the second state can be substantially proportional (e.g., within about ±25 percent) to the quantity of discrete inputs. For example, each discrete input can correspond substantially to a predetermined difference in volume. By way of a more specific example, each discrete input can correspond to about a 1 $cm^3$ difference in volume. Continuing with this example, a received 200 rewind command including three discrete inputs can produce about a 3 $cm^3$ difference between the first volume and the second volume. In this instance, updating 202 the display of the continuous surface on the graphical user interface can correspond to removing the most recent about 3 $cm^3$ of the volume of the progressive formation 194 of the continuous surface.

Additionally, or alternatively, the first state of the continuous surface and the second state of the continuous surface can correspond, for example, to partially overlapping time periods in the progressive formation of the continuous surface. By way of an illustrative example, the first state can correspond to a time period of 0 seconds to 45 seconds, and the second state can correspond to a time period of 0 seconds to 30 seconds. Thus, in this example, updating 202 the display of the continuous surface from the first state to the second state can produce a 15 second rewind.

The exemplary method 190 can optionally include storing 198 a plurality of temporal states of the continuous surface in a data structure. The temporal states can include, for example, the first state and the second state. More generally, however, the plurality of temporal states can correspond to states of the progressive formation 194 of the continuous surface. While the plurality of temporal states can correspond to the entire progressive formation 194 of the continuous surface, it should be appreciated that the plurality of temporal states can be selected to correspond only to significant changes in the progressive formation 194 of the continuous surface. Such selection of the temporal states can be useful, for example, for reducing the storage and/or processing requirements associated with updating 202 the display of the continuous surface. As a specific example, consecutive temporal states of the continuous surface stored 198 in the data structure can be distinguished from one another in the data structure by a key frame based on a change in the continuous surface as the continuous surface is progressively formed. Each key frame can, for example, correspond substantially to a predetermined change (e.g., about 1 $cm^3$) in volume defined by respective consecutive temporal states of the continuous surface. Thus, updating 202 the display of the continuous surface 202 can include moving from one key frame to another based on the received 200 rewind command (e.g., based on discrete inputs).

In certain implementations, the data structure can include respective pointers corresponding to the first state of the continuous surface and the second state of the continuous surface. In such implementations, updating 202 the display of the continuous surface from the first state to the second state can include changing from a first pointer corresponding to the first state to a second pointer corresponding to the second state. Such pointers can be useful for transitioning from the first state to the second state without necessarily requiring changes to the data structure and, thus, can facilitate rapid transitions with little computational overhead.

In some implementations, the data structure in which the plurality of temporal states of the continuous surface is stored can include a three-dimensional data structure (e.g., a three-dimensional grid) such as any one or more of the three-dimensional data structures described herein. Each state of the plurality of temporal states of the continuous surface can be derived from one or more portions of the three-dimensional data structure. The first state of the continuous surface can be derived from data (e.g., visited locations) in the three-dimensional data structure corresponding to a first time period associated with the first state and, similarly, the second state of the continuous surface can be derived from data (e.g., visited locations) in the three-dimensional data structure corresponding to a second time period associated with the second state. In this context, the derivation of the first state of the continuous surface and the second state of the continuous surface from data in the three-dimensional data structure can include any manner and form of generating the continuous surface, as described herein. Thus, updating 202 the display of the first continuous surface to the second continuous surface can include changing pointers to surface elements, or other types of elements, stored in the three-dimensional data structure and, additionally or alternatively, can include modifying the one or more entries of the three-dimensional data structure.

In instances in which the three-dimensional data structure includes surface elements, the first state of the continuous surface can be derived from the surface elements corresponding to visited locations of the catheter at the first time period and, similarly, the second state of the continuous surface can be derived from the surface elements corresponding to the visited locations of the catheter at the second time period. At least a portion of the second time period can precede at least a portion of the first time period. To the extent that such a difference between the first time period and the second time period corresponds to a difference in visited locations of the catheter, it should be appreciated that updating 202 the display of the continuous surface from the first state to the second state can, in some instances, result in fewer surface elements appearing in the second state of the continuous surface displayed on the graphical user interface. It should be further appreciated that, for the sake of clarity of explanation, the three-dimensional data structure has been described as including surface elements. The three-dimensional data structure can, additionally or alternatively, include one or more of zero-dimensional elements, one-dimensional elements, two-dimensional elements, three-dimensional elements, four-dimensional elements, and combinations thereof.

The exemplary method 190 can optionally include receiving 204 an undo command. Receiving 204 the undo command should be understood to be similar to receiving 184 the undo command described with respect to the exemplary method 170 (FIG. 7), unless otherwise indicated or made clear from the context.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals.

It will further be appreciated that a realization of the processes or devices described above may include computer-executable code created using a structured programming language such as C, an object oriented programming language such as C++, or any other high-level or low level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices.

In another aspect, any of the systems and methods described above may be embodied in any suitable transmission or propagation medium carrying computer-executable code and/or any inputs or outputs from same.

The method steps of the implementations described herein are intended to include any suitable method of causing such method steps to be performed, consistent with the patentability of the following claims, unless a different meaning is expressly provided or otherwise clear from the context. So, for example, performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims.

What is claimed is:

1. A method comprising:
   receiving a plurality of location signals, wherein
      each location signal is indicative of a respective location in three-dimensional space visited by a catheter in a cardiac chamber of a patient,
      each location signal includes at least one indication of chronological order of receipt, and
      the visited locations collectively indicate a size and shape of a volume defined by the cardiac chamber;
   storing the visited locations in entries in a three-dimensional (3D) data structure, wherein the entries define a boundary of the 3D data structure;
   progressively forming a continuous surface based on the boundary of the 3D data structure, wherein the continuous surface represents at least a portion of a blood-tissue boundary surface of the cardiac chamber;
   displaying the continuous surface on a graphical user interface;
   receiving, from an input device, a rewind command; and
   based on the rewind command—
      accessing one or more entries in the 3D data structure, wherein the one or more entries include an entry corresponding to a most recently visited location of the catheter, and wherein accessing the one or more entries includes removing one or more visited locations corresponding to the one or more entries and/or removing one or more indications of chronological order corresponding to the one or more entries, and updating a display of the continuous surface on the graphical user interface from a first state of the continuous surface to a second state of the continuous surface, at least a portion of the second state preceding at least a portion of the first state in the progressive formation of the continuous surface.

2. The method of claim 1, wherein the first state of the continuous surface and the second state of the continuous surface correspond to partially overlapping time periods in the progressive formation of the continuous surface.

3. The method of claim 1, wherein the first state of the continuous surface defines a first volume and the second state of the continuous surface defines a second volume different from the first volume.

4. The method of claim 1, further comprising storing a plurality of temporal states of the continuous surface in the 3D data structure, the plurality of temporal states of the continuous surface including the first state and the second state.

5. The method of claim 4, wherein, in the 3D data structure, consecutive temporal states of the continuous surface are distinguished from one another by a respective key frame based on a change in the continuous surface as the continuous surface is progressively formed.

6. The method of claim 5, wherein the continuous surface corresponding to each state of the plurality of states defines a respective volume, and each key frame corresponds substantially to a predetermined change in volume between respective consecutive temporal states of the continuous surface.

7. The method of claim 4, wherein the 3D data structure includes respective pointers corresponding to the first state of the continuous surface and the second state of the continuous surface, and displaying the second state of the continuous surface includes changing from a first pointer corresponding to the first state to a second pointer corresponding to the second state.

8. The method of claim 4, wherein each state of the plurality of temporal states of the continuous surface is derived from one or more portions of the 3D data structure.

9. The method of claim 1, wherein progressively forming the continuous surface is based, at least in part, on a chronological order of receipt of the one or more signals indicative of the respective visited locations of the catheter in the cardiac chamber.

10. The method of claim 1, further comprising receiving an undo command and, based on the undo command, modifying the display of the continuous surface on the graphical user interface from the second state of the continuous surface to a third state of the continuous surface, wherein the third state of the continuous surface follows the second state of the continuous surface in the progressive formation of the continuous surface.

11. The method of claim 10, wherein the third state of the continuous surface precedes or is substantially contemporaneous with the first state of the continuous surface in the progressive formation of the continuous surface.

12. The method of claim 1, wherein receiving the rewind command includes receiving a signal indicative of a quantity of discrete inputs, and a quantity of the one or more accessed entries of the data structure is proportional to the quantity of the discrete inputs.

13. The method of claim 1, wherein receiving the rewind command includes displaying, on the graphical user interface, visual indicia of the received rewind command.

14. A non-transitory, computer-readable storage medium having stored thereon computer executable instructions that, when executed by a computing system, cause the computing system to perform operations comprising:

receiving a plurality of location signals, wherein
each location signal is indicative of a respective location in three-dimensional space visited by a catheter in a cardiac chamber of a patient,
each location signal includes at least one indication of chronological order of receipt, and
the visited locations collectively indicate a size and shape of a volume defined by the cardiac chamber;

storing the visited locations in entries in a three-dimensional (3D) data structure, wherein the entries define a boundary of the 3D data structure;

progressively forming a continuous surface based on the boundary of the 3D data structure, wherein the continuous surface represents at least a portion of a blood-tissue boundary surface of the cardiac chamber;

displaying the continuous surface on a graphical user interface;

receiving, from an input device, a rewind command; and based on the rewind command— accessing one or more entries in the 3D data structure, wherein the one or more entries include an entry corresponding to a most recently visited location of the catheter, and wherein accessing the one or more entries includes removing one or more visited locations corresponding to the one or more entries and/or removing one or more indications of chronological order corresponding to the one or more entries, and updating a display of the continuous surface on the graphical user interface from a first state of the continuous surface to a second state of the continuous surface, at least a portion of the second state preceding at least a portion of the first state in the progressive formation of the continuous surface.

* * * * *